(12) United States Patent
Salvetti et al.

(10) Patent No.: US 6,509,150 B1
(45) Date of Patent: Jan. 21, 2003

(54) COMPOSITIONS AND METHODS FOR RECOMBINANT ADENO-ASSOCIATED VIRUS PRODUCTION

(75) Inventors: Anna Salvetti, Nantes (FR); Pascale Nony, Nantes (FR); Gilliane Chadeuf, Nantes (FR); Philippe Moullier, Basse Goulaine (FR)

(73) Assignee: Universite de Nantes, Nantes (FR)

( * ) Notice: Subject to any disclaimer, the term of this patent is extended or adjusted under 35 U.S.C. 154(b) by 0 days.

(21) Appl. No.: 09/263,093

(22) Filed: Mar. 5, 1999

(51) Int. Cl.[7] ................... C12N 15/861; C12N 15/864; C12N 15/63; C12Q 1/68; C12Q 1/70
(52) U.S. Cl. ................. 435/5; 435/235.1; 435/320.1; 435/325; 435/6; 435/7.1; 435/455; 435/456; 435/457; 435/465; 435/366; 435/239; 435/373
(58) Field of Search ................ 435/235.1, 320.1, 435/325, 5, 6, 7.1, 455, 456, 457, 465, 366, 239

(56) References Cited

U.S. PATENT DOCUMENTS 5,962,313 A * 10/1999 Podsakoff et al. ....... 435/320.1
6,004,797 A * 12/1999 Colosi ..................... 435/235.1

FOREIGN PATENT DOCUMENTS

| EP | 0 856 585 A1 | 8/1998 |
|---|---|---|
| WO | 97/06272 | 2/1997 |
| WO | 97/08298 | 3/1997 |

OTHER PUBLICATIONS

Salvetti et al., Human Gene Therapy, vol. 9, pp. 695–706, Mar. 1998.*
Douglas M. McCarty et al., "Identification of Linear DNA Sequences That Specifically Bind the Adeno–Associated Virus Rep Protein," Journal of Virology, V. 68, 1994, pp. 4988–4997.
Xu–Shan Wang, "Characterization of Wild–Type Adeno–Associated Virus Type 2–Like Paricles Generated during Recombinant Viral Vector Production and Strategies for Their Elimination," V. 72, 1998, pp. 5472–5480.
Anna Salvetti et al., "Factors Influencing Recombinant Adeno–Associated Virus Production," Human Gene Therapy, V. 9, 1998, pp. 695–706.

* cited by examiner

*Primary Examiner*—David Guzo
(74) *Attorney, Agent, or Firm*—Young & Thompson

(57) ABSTRACT

The present invention relates to methods and compositions for the production of recombinant Adeno-Associated Viruses (rAAV). In particular, the invention discloses nucleic acid constructs and packaging cells having improved properties for rAAV production, as well as novel methods of titration and characterization of rAAV preparations. The invention also describes novel sequences which promote or increase the packaging of nucleic acids in rAAV, and their use for producing rAAV with high efficiency. The invention can be used for producing or testing high quality rAAV preparations, for biological, preclinical, clinical or pharmaceutical uses.

24 Claims, 10 Drawing Sheets

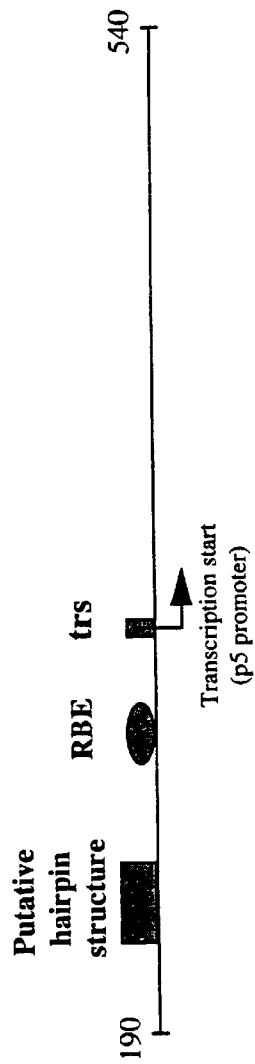
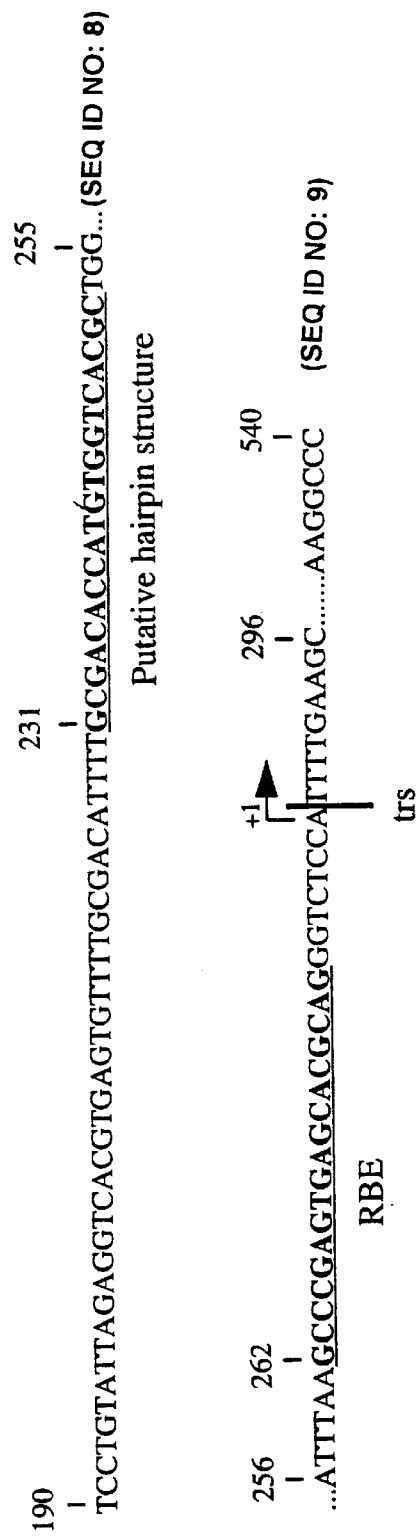
FIGURE 8A
FIGURE 8B

SEQUENCE LISTING

<160> NUMBER OF SEQ ID NOS: 9

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: RES

<400> SEQUENCE: 1
gcccgagtga gcacgcag                                                 18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: RES variant

<400> SEQUENCE: 2
gcgacaccat gtggtcacgc                                               20

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: RES

<400> SEQUENCE: 3
gcccgagtga gcacgcaggg tctccatttt gaa                                33

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 4
atgatttaaa tcaggttggg ctgccg                                        26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 5
gctctagatg agcttccacc actgtc                                        26

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
tatttaagcc cgagtgagca                                               20

<210> SEQ ID NO 7
<211> LENGTH: 20

```
<212> TYPE: DNA
<213> ORGANISM: Artificial Sequence
<220> FEATURE:
<223> OTHER INFORMATION: Description of Artificial Sequence: primer

<400> SEQUENCE: 7
aaagttctca ttggtccagt                                               20

<210> SEQ ID NO 8
<211> LENGTH: 62
<212> TYPE: DNA
<213> ORGANISM: Artificial Sequence
<220> FEATURE:
<223> OTHER INFORMATION: Description of Artificial Sequence: RES element

<400> SEQUENCE: 8
tcctgtatta gaggtcacgt gagtgttttg cgacattttg cgacaccatg tggtcacgct    60
gg                                                                  62

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: RES element

<400> SEQUENCE: 9
atttaagccc gagtgagcac gcagggtctc cattttgaag caaggccc                48
```

COMPOSITIONS AND METHODS FOR RECOMBINANT ADENO-ASSOCIATED VIRUS PRODUCTION

The present invention relates to methods and compositions for the production of recombinant Adeno-Associated Viruses (rAAV). In particular, the invention discloses nucleic acid constructs and packaging cells having improved properties for rAAV production, as well as novel methods of titration and characterization of rAAV preparations. The invention also describes novel sequences which promote or increase the packaging of nucleic acids in rAAV, and their use for producing rAAV with high efficiency. The invention can be used for producing or testing high quality rAAV preparations, for biological, preclinical, clinical or pharmaceutical uses.

BACKGROUND AND INTRODUCTION

Wild type Adeno-Associated Virus (wtAAV) is a naturally defective parvovirus which requires co-infection with a helper virus, such as adenovirus or herpes virus, in order to establish a productive infection. The virus is not associated with any human disease and has been shown to have a broad host range of infection in vitro. AAV has a relatively simple genome organization composed of two major genes coding for the regulatory (rep) and structural (cap) proteins. Three viral promoters located at map unit 5 (p5), 19 (p19) and 40 (p40) control the synthesis of mRNA coding for the four Rep and the three Cap proteins. The viral genome is flanked by 145 bases inverted terminal repeats (ITRs) which contain palindromic sequences necessary in cis for replication of the viral genome (Leonard and Berns, 1994).

Recombinant AAV viruses (rAAV) are derived by deleting the rep and cap genes which are replaced by the transgene and the transcriptional control elements needed for its expression. The only viral sequences retained in cis are the viral ITRs (Muzyczka, 1992). The ability of rAAV to efficiently transduce tissues in mice such as the muscle, the retina or the liver (Fisher et al., 1997; Flannery et al, 1997; Kessler et al., 1996; Koeberl et al., 1997; Snyder et al., Herzog et al., 1997; 1997; Xiao et al., 1996; Zolotukhin et al, 1996) and to lead to a prolonged gene expression with little to no pathology makes this virus unique among the family of viral vectors. In this respect, rAAV can be used in vitro for recombinant protein production, gene regulation studies, AAV protein production (to be used in non-viral gene delivery systems), etc. rAAV can also be used ex vivo or in vivo, to deliver genes of interest for biological, toxicological, prophylactic or therapeutic indications for instance. In this regard, it should be noted that several clinical trials are currently ongoing using a rAAV gene delivery vector.

However, widespread use of rAAV is hampered by the relatively cumbersome and inefficient procedure needed to produce it at high titers and in sufficient amount and quality. The standard procedure relies upon the transfection of 293 cells with two plasmids: a plasmid providing in trans the rep and cap functions, and the rAAV vector plasmid itself. After subsequent infection with an adenovirus, rAAV particles are assembled in the nuclei of the cells concomitantly with adenoviral particles. rAAV stocks are obtained after purification from total cell lysates through CsCl gradients (Snyder et al., 1996).

However, these methods represent relatively long and complex procedures, which cannot be easily scaled-up. Furthermore, because of the number of constructs required, recombination events have been observed leading to rAAV preparations which are contaminated with replicating AAV particles and with adenoviruses. There is therefore a need for improved methods of producing rAAV, for biological, preclinical, clinical or pharmaceutical uses. In particular, there is a need for methods of producing rAAV preparations with high titers of infectious particles and which are essentially free of adenoviruses. There is also a need for methods to produce rAAV preparations with significantly reduced contamination by replication competent or recombined AAV. There is also a need for improved methods of titration of rAAV preparations, and for methods of characterization of such preparations, i.e., for use in Quality Control steps, as well as for detecting rAAV or contaminants in biological fluids, for instance.

The present invention now provides novel methods and compositions for producing and characterizing rAAV preparations. In particular, the invention provides methods of producing rAAV with very high yields of infectious particles and essentially free of detectable adenovirus contamination.

DESCRIPTION OF THE INVENTION

The present invention relates to compositions and methods for producing and/or characterizing rAAV preparations of improved quality. The invention relates more particularly to improved nucleic acid constructs that provide for an efficient production of rAAVs, as well as to compositions, cell lines and methods for characterizing rAAV preparations. The invention can be used to produce rAAV for biological, preclinical or clinical uses, e.g., pharmaceutically acceptable rAAV preparations.

Within the context of the present invention, a recombinant Adeno-Associated Virus (rAAV) designates an AAV virus which comprises at least a recombinant nucleic acid genome. More specifically, rAAVs generally comprise a recombinant genome lacking a functional rep and/or cap region, and comprising a heterologous nucleic acid. Most conventional rAAVs comprise a recombinant genome lacking the entire Rep and Cap regions, which are replaced by the heterologous nucleic acid. Such recombinant genomes thus usually comprise the heterologous nucleic acid flanked by the left and right Inverted Terminal Repeats of AAV. rAAVs may comprise additional modifications, such as artificial or heterologous capsid proteins, for instance. Furthermore, the recombinant genome may comprise, in replacement or in addition to ITR sequence, RES elements as disclosed in the present invention. rAAVs may be derived from different serotypes of AAV, such as for instance AAV-2, AAV-3, AAV-4 or AAV-6.

In the present invention, except otherwise indicated, all references to nucleotide positions of the AAV genome are made with respect to the sequence of wild-type AAV-2 available at Genebank under number AF043303.

A recombinant Adeno-Associated Virus vector plasmid (rAAV vector plasmid) designates a nucleic acid construct comprising a copy of the genetic information to be packaged into AAV capsids, to form the rAAV. The rAAV vector plasmid is therefore any nucleic acid construct comprising the recombinant genome of the rAAV as defined above, preferably a heterologous nucleic acid flanked by one or two AAV Inverted Terminal Repeats (ITR) and/or, optionally, one or several RES elements. The rAAV vector plasmid can be autonomously replicating, conditionally replicating, or stably integrated into the genome of the packaging cell.

A rep-cap plasmid designates any nucleic acid construct encoding the rep and/or cap proteins, which provide in trans the AAV complementing functions lacking in the rAAV vector plasmid. Generally, the rep-cap plasmid encodes Rep78, Rep68, Rep52, Rep40, VP1, VP2 and VP3. The rep-cap plasmid can be a single construct encoding all the required REP and CAP proteins, under the control of the same or separate promoters. The rep-cap plasmid can also be a mixture of distinct nucleic acid constructs encoding one or several REP and CAP proteins. The rep-cap plasmid can be autonomously replicating, conditionally replicating, or stably integrated into the genome of the packaging cell.

As indicated above, a first aspect of the invention resides in a method of characterizing rAAV preparations or stocks. Indeed, because of the complex methods and constructs needed to produce rAAV, it is important to have efficient and accurate methods of characterizing the rAAV preparations obtained, especially for biological uses. Previous methods known in the art essentially focus on the determination of the contamination by adenoviruses, and/or the number of infectious AAV particles. Also, in determining the number of infectious rAAV particles, most prior art methods rely on the detection of the expression product of the nucleic acid inserted in the rAAV genome and are therefore transgene-dependent. The invention now provides a new method of characterizing rAAV preparations, which is transgene-independent, sensitive, accurate, and allows the measure of adenovirus and recombined AAV contaminants. This method can be used in any rAAV production method, or as a Quality Control in biological processes, to check the quality of a preparation and, optionally, allow the improvement of the production parameters.

More specifically, an object of the present invention is a method of characterizing a rAAV preparation, said method comprising:

a) contacting a sample of said preparation with a culture of cells expressing the rep proteins, b) contacting a sample of said preparation with a culture of cells expressing the rep proteins, co-infected with an adenovirus, and c) contacting a sample of said preparation with a culture of cells which do not express Rep proteins, co-infected with an adenovirus, and measuring the presence of viruses in cultures a), b) and c).

As will be discussed in more details below, the rAAV preparation can be any preparation of rAAVs produced by any method. It is, preferably, a purified rAAV stock obtained from a rAAV producing cell culture extract. The rAAV preparation can be for instance a stock of rAAVs, to be assayed before administration to a mammalian, including a human being, for clinical or pharmaceutical purposes. In this regard, "characterizing" means within the context of the above method, determining both (i) the number of infectious rAAV particles and (ii) the presence of contaminating viruses, in particular contaminating adenoviruses and rep-positive rAAVs in the preparation.

In the characterization method of this invention, the sample being contacted with the above indicated cell cultures can be a pure or a diluted sample of the rAAV preparation. In a preferred embodiment, serial dilutions of the rAAV preparation are being used, comprising for instance from about $5.10^4$ to 50 infectious particles/ml.

For carrying out the claimed method, different cell cultures can be used. Preferably, of course, the cells are permissive to AAV, i.e., can replicate the AAV genome in appropriate conditions (i.e., in the presence of adenoviral helper functions). Suitable cell cultures include culture of human primary or established cell lines, preferably established cell lines; other mammalian cell lines or cultures, including canine or murine cells. Example of cells which can be used include for instance human cells such as nervous cells, fibroblasts, hepatocytes, myoblasts or the like preferably established as cell lines. More preferred cell lines include the HEK cells, Hela cells, Huh7, HT1080, J82 or T98G, for instance.

In conducting the method of this invention, it is preferred to use in all three contacting tests the same cell type (i.e., HT1080, Huh7, HeLa cells, etc.). In a preferred embodiment, the cell culture used in a), b) and c) is a culture of HeLa cells.

In an even more preferred embodiment, the cell cultures used in a) and b) are cultures of the same cell populations. More preferably, the cell culture used in c) is also essentially identical to those used in a) and b), except for the Rep status.

As explained above, the cells used in a) and b) express the Rep proteins, i.e. the proteins of AAV which are involved in the replication of the genome. The Rep region of AAVs produces essentially 4 major proteins, Rep78, Rep 68, Rep 52 and Rep 40. All these proteins are involved in the replication of AAVs and should be present in the cell culture, to ensure maximum efficacy. Accordingly, in a particular embodiment, the cells expressing AAV rep proteins used in the invention are cells which express Rep78, Rep 68, Rep 52 and Rep 40. Preferably, the Rep proteins are expressed under the control of the AAV p5 and p19 promoters. In a more particular embodiment, the cells express the AAV Rep proteins encoded by nucleotides 190–2278 of the AAV genome. Alternative embodiments use cells which express only some of the AAV rep proteins, such as Rep78/Rep68, for instance, which are known to be essential for replication, or any other combination thereof which allows replication of AAV genome.

In addition, in the method of this invention, it is preferred to use cells which also express AAV cap proteins, i.e., the proteins of AAV involved in the formation of the capsid. The Cap proteins (VP1, VP2 and VP3) are encoded by nucleotides 1850–4484 of AAV. These proteins can be expressed under the control of the natural AAV p40 promoter, or any heterologous promoter. Preferably, cells used in a) and b) also express the AAV Cap protein expressed by nucleotides 1700–4484 of the AAV genome.

In a variant, the invention relates to a method of characterizing a rAAV preparation, said method comprising:

a) contacting a first sample of said preparation with a culture of mammalian cells expressing the AAV rep proteins encoded by nucleotides 190–2278 of the AAV genome, b) contacting a second sample of said preparation with another culture of the cells of a), co-infected with an adenovirus, and c) contacting a third sample of said preparation with a culture of mammalian cells which do not express Rep proteins, co-infected with an adenovirus, and measuring the presence of viruses in cultures a), b) and c).

More preferably, the mammalian cells in a) and b) above also express the AAV Cap proteins encoded by nucleotides 1850–4484 of the AAV genome. In a particularly preferred embodiment, the mammalian cells used in a) and b) comprise a nucleic acid sequence, integrated in their genome, which codes for the Rep and Cap proteins of AAV. The nucleic acid has for instance the sequence of nucleotides 190–4484 of the AAV genome. More preferably, the mammalian cells in a), b) and c) are HeLa cells, such as cells HeLaRC32, disclosed in the Examples.

In assays b) and c) of the instant method, the cell cultures are co-infected with an adenovirus. Usually, the adenovirus is of the group C, even more preferably of the serotype Ad2, Ad5, Ad7 or Ad12. Other types of adenoviruses can be used, such as for instance canine adenoviruses (CAV-2) which are known to complement AAV replication. Furthermore, the adenovirus can be wild-type or modified, in particular temperature sensitive. The doses of adenoviruses used can be adapted by the skilled artisan, depending on the cell types, the rAAV preparation, and the nature of the adenovirus. Generally, the adenovirus is used at an MOI of between 5 and 1000, preferably below 800, more preferably between 50 and 600. Finally, the adenovirus can be replaced with an adenoviral plasmid, i.e. a plasmid or combination of plasmids encoding the adenoviral functions necessary for AAV replication, although the use of a virus is preferred.

After the contacting of the rAAV preparation with the cell cultures, the presence of viruses is determined. In this regard, the measuring comprises measuring the presence of rAAV viruses within each test a), b) and c). More preferably, the measuring of the presence of viruses in cultures a), b) and c) comprises measuring (i.e., detecting) the presence of rAAV replicating DNA in the cells. This measure is usually accomplished by using rAAV-specific probes, optionally after amplification of the cellular nucleic acids with rAAV-specific primers. In a particular embodiment, a probe is used which is complementary to all or part of the rAAV genome, in particular to all or part of the heterologous nucleic acid present in the rAAV genome. The probe comprises preferably at least 100 bp, to ensure higher selectivity. The probe can be labeled with any conventional technique (enzymatic, fluorescent, radioactive, etc.). In a preferred embodiment, the detection of the presence of rAAV replicating DNA in the cells of a), b) and c) is performed after cell lysis without amplification of the cellular nucleic acids. Detection without amplification allows a better quantitative evaluation of the number of rAAV genomes present within the cells. Of course, amplification can be performed, prior to the detection, by using primers specific for regions of the heterologous nucleic acid present in the rAAV genome.

The detection of rAAV DNA within the cells is preferably accomplished by hybridization of the cellular nucleic acids with a probe as defined above. Preferably, the hybridization is performed on a solid support, such as a membrane, filter, etc., onto which the cellular nucleic acids have been transferred or onto which the cells have been directly lysed. The hybridization conditions can be either medium or, preferably, of high stringency. Typical hybridization conditions under high stringency are as follows: Dextran sulfate 5%, SSC 5%, SDS 0.1% liquid block 10%, (Amersham). The support is prehybridized 30' at 65° C., and the denatured probes are then hybridized overnight at 65° C. It should be understood that the hybridization conditions can be adjusted, for instance by reducing the temperature or the washing conditions, by the skilled artisan.

Generally, the measure is performed 12–96 hours after the contacting, preferably less than 48 hours. Typically, when measuring comprises measuring the AAV replicating nucleic acids within the cell culture, the measuring is performed at about 24 hours post-contacting. It allows replication, but no release of AAV which could infect other cells.

The above method is particularly advantageous since it provides not only the titer of a preparation in infectious particles, regardless of the nature of the heterologous nucleic acid contained in the vector, but also the level of contamination by adenoviruses and rep-positive AAVs.

Indeed, the contacting with cell culture a), i.e., with a cell culture expressing rep proteins but in the absence of helper adenovirus functions, allows the identification of the presence of complementing adenoviruses within the rAAV preparation, i.e., the presence of contaminating adenoviruses. Indeed, it is known that AAV cannot replicate their genome in the absence of helper adenovirus functions. In this cell culture a), the replication of rAAV implies the presence of helper adenoviral function in the medium, i.e., of contaminating adenoviruses within the preparation. The number of cells in which rAAV is replicating can be directly correlated to the level of adenovirus contamination.

The contacting with cell culture b), i.e., with a cell culture expressing rep proteins, in the presence of helper adenovirus functions, allows the titration of infectious rAAV particles present in the preparation.

The contacting with cell culture c), i.e., with a cell culture which do not express rep proteins, in the presence of helper adenovirus functions, allows the identification of the presence of rep-positive AAV viruses within the rAAV preparation, i.e., the presence of contaminating rAAV which contain a rep-encoding nucleic acid or a rep protein.

The method is therefore very efficient and provides immediate information regarding the quality of a rAAV preparation, as illustrated in the Examples. Another object of the present invention therefore lies also in a method as described above, for detecting the presence of rAAV and/or rep-positive AAVs and/or adenoviral particles in biological fluids, in particular after in vivo administration of rAAV preparations in animals and/or human subjects. Such biological fluids are, more particularly, serum, urine, stool, saliva, broncho alveolar fluids, etc. The method is performed as described above, by contacting, in tests a), b) and c), samples of the biological fluids or dilutions or concentrates or derivatives thereof. It can thus be used to monitor safety issues during preclinical, clinical or pharmaceutical settings.

Furthermore, the above method allowed the inventors to establish improved conditions and improved nucleic acid constructs for producing rAAV stocks. Moreover, in performing the above characterization method, the inventors discovered the presence of rep-positive AAVs within the preparation, which led them to try to understand the molecular mechanisms responsible therefor. Indeed, because the nucleic acid constructs used in the production method are essentially free of overlapping regions between each other, homologous recombination events are essentially impossible. Non-homologous recombination events between the rep-cap plasmid and the rAAV vector plasmid might account for the presence of such rep-positive rAAVs in the final preparation. Surprisingly, the applicants found that the presence of rep-positive particles could be the result of an ITR-independent packaging of rep nucleic acid. Surprisingly, the inventors have now discovered the existence of non-ITR packaging regions within the AAV genome. Both the improved method and non-ITR packaging regions are also encompassed by the present application, as will be discussed below.

The invention therefore relates also to a method of producing rAAV preparations, comprising:
   a) producing rAAVs in a cell culture expressing the Rep and Cap functions and the adenovirus helper functions, and
   c) characterizing the rAAVs produced according to the method disclosed above.

More preferably, the method comprises:
   a) producing rAAVs in a cell culture expressing the Rep and Cap functions and the adenovirus helper functions,
   b) purifying the rAAVs produced, and
   c) characterizing the rAAVs produced according to the method disclosed above.

The production of the rAAVs can be performed according to various methods, including conventional methods known in the art. For instance, step a) can be accomplished by co-transfection of a cell culture with a Rep-Cap plasmid, the rAAV vector plasmid and a helper adenovirus. Step a) can also be performed using a culture of cells which contain, stably integrated into their genome, nucleic acid construct(s) encoding the Rep and/or Cap proteins. Also, the helper adenovirus can be either wild-type adenovirus, or a replication deficient adenovirus, such as a E1-deficient adenovirus, for instance. In this embodiment, the cells used preferably produce the function(s) lacking in the adenovirus. In particular, the 293 cells are frequently used, which express the E1 functions of adenoviruses.

In a particular embodiment, in the producing step a), a rep-cap plasmid is used, which lack any functional ITR region, in particular any adenoviral ITR region. In this respect and, contrary to previous observations, the inventors have now shown that the use of a rep-cap plasmid containing the adenoviral ITR regions does not increase the yield of infectious particles. It is therefore a preferred embodiment of this invention to use a Rep-Cap plasmid lacking adenoviral ITR regions. Such plasmids are disclosed in the examples. In particular, a preferred Rep-Cap plasmid within the context of the instant invention is a plasmid containing a Rep-Cap unit consisting of residues 190–4484 of the AAV genome or fragments thereof encoding functional Rep and Cap proteins. Furthermore, the plasmids used may contain the homologous transcriptional promoter regions of the AAV Rep and Cap genes (i.e., promoters p5, p19 and p40), or any heterologous promoter region. Particular examples of such plasmids are, for instance:

plasmid pspRC, which contains the ITR-deleted AAV genome position 190–4484 (FIG. 1), and plasmid pspRCC, which contains the rep gene (190–2278 bp of wtAAV) followed by the bGH polyadenylation signal and the CMV promoter leading the expression of the cap ORF (1882–4484 bp of wtAAV).

In this regard, a particular object of this invention also resides in plasmids pspRC and pspRCC.

In another particular embodiment of this invention, step a) comprises the co-transfection of a cell culture with a rep-cap plasmid, a rAAV vector plasmid and a helper adenovirus.

In a further particular embodiment of the present invention, step a) comprises the use of adenovirus helper plasmids, instead of a helper adenovirus. Indeed, as indicated before, while the production of rAAV requires the presence of adenovirus helper functions, the use of a helper adenovirus generally leads to a contamination of rAAV preparations by adenoviruses (defective, replicating and/or wild-type). In order to avoid such a contamination, the inventors have now found that adenovirus plasmids can be used, without significantly affecting the yields of rAAV produced. In this respect, particular plasmids can be used, such as plasmids carrying the entire adenoviral genome or portions thereof, which are sufficient to supply the functions required for rAAV production. In a particular embodiment, a plasmid is used carrying the entire adenovirus genome. Such a plasmid is for instance pAdc disclosed on FIG. 1. In another particular embodiment, a plasmid is used, which contains the adenoviral genome lacking the left and right ITRs and the packaging region. In a further preferred embodiment, a plasmid is used, which contains a defective adenoviral genome lacking the left and right ITRs, the packaging region and the E1 region. Such a plasmid is, for instance plasmid pAdΔ (FIG. 1).

Surprisingly, the inventors have now shown, for the first time, that the use of such plasmids in replacement of a helper adenovirus does not reduce the yields of infectious rAAV particles produced. Furthermore, the use of such plasmids avoids the production of contaminating adenoviruses in the preparations, as demonstrated in the examples. This embodiment thus represents a preferred way of carrying out the instant invention.

In this regard, a particular object of this invention also resides in plasmids pAdc and pAdΔ.

Another object of this invention also resides in a method of producing rAAVs comprising:

(i) co-transfecting a cell culture with:
 a rAAV vector plasmid,
 a Rep-Cap plasmid devoid of ITR, containing preferably a Rep-Cap unit consisting of residues 190–4484 of the AAV genome or fragments thereof encoding functional Rep and Cap proteins, and
 an adenovirus plasmid containing the entire adenoviral genome or a genome lacking the left and right ITRs, the packaging region and, optionally, the E1 region, and (ii) recovering the rAAV produced.

In another particular embodiment of the present invention, step a) above comprises the use of a culture of cells which contain, in their genome, nucleic acid construct (s) encoding the rep and/or cap functions, preferably the rep and cap functions. In this embodiment, the production step a) comprises the co-transfection of this cell culture with the rAAV vector plasmid and with a helper adenovirus or an adenovirus plasmid as described above. This embodiment is advantageous in that it avoids the need for a Rep-Cap plasmid. Suitable cells for carrying this embodiment include any cells encoding the AAV REP and CAP proteins encoded by nucleotides 190–4484 of the AAV genome. These cells can be derived, as disclosed above, from human cells, such as embryonic cells, or even from other mammalian cells. Preferred cells are obtained from 293 cells, HeLa cells, A549 cell, Huh7 cells, HT1080, J82, T98G or HER cells. A specific example is the HeLaRC32 cells disclosed above, for instance.

Another object of this invention therefore resides also in a method of producing rAAVs comprising (i) co-transfecting a culture of cells which contain, in their genome, nucleic acid construct(s) encoding the rep and/or cap functions, preferably the rep and cap functions, with:
 a rAAV vector plasmid, and
 a helper adenovirus or an adenovirus plasmid containing the entire adenoviral genome or a genome lacking the left and right ITRs, the packaging region and, optionally, the E1 region, and (ii) recovering the rAAV produced.

Step b) of the above production method comprises the purification of the rAAV produced. Said purification can be performed according to various techniques, including methods known in the art such as centrifugation, clarification, and cesium chloride gradient purification. In this regard, the CsCl purification procedure disclosed in the art essentially comprises the centrifugation of the rAAV cell extract at 41 000 rpm for 48 hours (rotor sw41). The inventors have now shown that it is possible to significantly reduce the length of the centrifugation step, when the other parameters are adjusted. In particular, the inventors have now shown when the CsCl centrifugation is maintained for 6 hours at between 60 000 and 70 000 rpm, preferably between 65 000 and 70 000 rpm, the same level of purity is obtained than with previous methods, requiring 48 hours centrifugation.

A preferred embodiment of the invention therefore comprises centrifuging the rAAV preparation in a cesium chloride gradient for less than 12 hours, at between 60 000 and 70 000 rpm, preferably between 65 000 and 70 000 rpm.

Other purification methods can be used such as, in particular, chromatographic techniques. In this respect, a particular purification method uses anion exchange chromatography, optionally combined to exclusion chromatography. A specific purification protocol comprises for instance the loading of the rAAV preparation on an anionic exchange chromatography column, such as for instance Resource Q (Amersham, Pharmacia Biotech), followed by an exclusion chromatography, for instance onto a Sephacryl (S500) column, to exclude the viral particle and separate them out of residual protein and lipid contaminants.

A particular object of the present invention therefore also lies in a method of purifying rAAVs from a biological sample, comprising treating said sample in a cesium chloride gradient centrifugation at between 60 000 and 70 000 rpm, preferably for less than 12 hours, and recovering the fraction(s) containing the purified rAAVs.

Another particular object of this invention lies in a method of purifying rAAVs from a biological sample, comprising treating said sample at least by anion exchange chromatography and exclusion chromatography.

Furthermore, as indicated above, the invention also relates to novel nucleic acids with packaging activity. Indeed, the inventors have now discovered that nucleic acid regions, distinct from the ITRs, can mediate and/or increase the packaging of nucleic acids within AAV capsids. These regions, termed "Replication Encapsidation Sequence" or "RES" as well as their use for producing rAAVs, represent another particular object of the instant invention.

More particularly, within the context of the present invention, a "Replication Encapsidation Sequence" represents a sequence different from an AAV ITR sequence, which promotes and/or facilitates the packaging of a nucleic acid into an AAV capsid. Preferably, a RES element comprises a Rep Binding Element (RBE), where Rep78/Rep68 proteins can bind, and a terminal resolution site (trs), for the binding of endonucleases. Even more preferably a RES comprises a RBE site, a trs site and a palindromic sequence. Surprisingly, the Applicants have now found that regions favoring packaging of a nucleic acid into an AAV particle are present in the genome of viruses, such as AAV. These regions are distinct from the ITRs, and can promote the packaging of an ITR-free nucleic acid into an AAV particle. The invention therefore discloses new nucleic acids with packaging activity, that can be used to package nucleic acids into AAV capsids, or to improve the packaging efficiency of conventional rAAV vectors.

A particular object of this invention lies in an isolated Replication Encapsidation Sequence, wherein said RES is a nucleic acid sequence distinct from an AAV ITR sequence, which provides or promotes the packaging of a nucleic acid operably linked thereto into an AAV particle.

Preferably, a RES of this invention comprises a Rep Binding Element and a terminal resolution site, and, optionally, a palindromic sequence. A preferred RES according to this invention is an isolated nucleic acid, wherein, said nucleic acid provides or promotes the packaging of a polynucleotide operably linked thereto into an AAV particle.

A particular example is a RES comprising a region having the sequence of SEQ ID NO: 1 (GCC CGA GTG AGC ACG CAG) or a functional variant thereof.

More preferably, a RES of this invention comprises a region having the sequence of SEQ ID NO: 1 or a functional variant thereof and further comprises a region having the sequence of SEQ ID NO: 2 (GCG ACA CCA TGT GGT CAC GC) or a functional variant thereof.

A particular RES of this invention is a nucleic acid comprising SEQ ID NO: 3 (GCC CGA GTG AGC ACG CAG GGT CTC CAT TTT GAA) or a functional variant thereof, which nucleic acid having a packaging activity.

Even more preferably, a RES of this invention comprises SEQ ID NO: 3 or a functional variant thereof and SEQ ID NO: 2 or a functional variant thereof.

The term "functional variant" means any sequence comprising one or several structural modifications, that still retain the activity of the sequence, i.e., the binding to Rep78 or Rep68 for SEQ ID NOS: 1 and 3, and the ability to form a hairpin structure for SEQ ID NO: 2. More preferred functional variants retains at least 50% identity with the sequence disclosed in the examples. Particular examples of functional variants are sequences with one or several mutations, additions or deletions in the above sequences, in particular 1, 2 or 3 mutations.

Other typical variants are sequences which hybridize with the above sequences and retain the RES activity. To search for sequences in the genome of other viruses having some homologies with the RES fragment and be considered as variants, hybridization in low stringency conditions using the RES fragment as a probe are performed. As an example, hybridization is done overnight at 56° C. instead of 65° C. in the hybridization solution recommended by the manufacturer's instructions (Amersham), which is 5×SSC, 0.1% (W/V) SDS, 5% (W/V) Dextran sulphate and 1/20 of liquid block. Washes are performed also in low stringency conditions, for instance: 1×SSC, 0.1% SDS at 56° C. The RES can be artificial, semi-synthetic, viral or of any other origin.

Other functional variants are RES sequences derived from other parvoviruses which exhibit the functional properties of the above RES sequences.

Preferably, RES elements contain less than 400 bp. A specific example is provided on FIG. 8A, which consists of nucleotides 190–540 of AAV genome (i.e., 350 bp). Fragments of this RES are presented in FIG. 10, which represent particular embodiments of this invention, such as nucleotides 190–350, 230–350, 230–300, 250–300 or functional variants thereof, for instance.

As indicated above, the RES elements of this invention can be used either to promote the packaging of a nucleic acid into an AAV capsid, or to improve the packaging efficiency of rAAV vector plasmids. Accordingly, a particular object of this invention is a nucleic acid consisting of one or several RES elements fused to a heterologous polynucleotide lacking a functional ITR sequence.

The heterologous polynucleotide lacking a functional ITR sequence can be any nucleic acid sequence of interest, such as a nucleic acid coding for a protein or RNA of interest for instance. Fused means that the two elements are operably linked together, in the same or reverse orientation. The RES elements can be fused at the 5' or 3' ends of the heterologous nucleic acid, or inserted within said polynucleotide. Examples of such nucleic acids include for instance plasmid RES+CMV-LacZ or plasmid RES-CMV-LacZ as shown on FIG. 9. Any similar construct in which the CMV promoter is replaced with another promoter and/or the LacZ gene is replaced with another gene can be produced by the skilled artisan.

Another object of this invention is a rAAV vector plasmid, comprising a recombinant AAV genome and one or several RES element. A particular construct is, for instance, a plasmid comprising the following operably linked elements: 5'-ITR-RES-heterologous polynucleotide-ITR-3'.

The invention also relates to a rAAV particle comprising a recombinant nucleic acid genome, wherein said recombinant nucleic acid genome comprises one or several RES elements.

The invention can be used to produce rAAV and to characterize rAAV preparations, for use in various technical areas, such as experimental biology, preclinical studies, clinical studies or pharmaceutical indications.

Other advantages and uses of the present invention be disclosed in the following experimental section, which should be regarded as illustrative and not limitative.

Legend to the Tables

TABLE 1. Characterization of the 18 large scale rAAV stocks. Each vector was produced from 25 15-cm plates of 293 cells except for stocks marked with an asterisk which were produced from 50 15-cm plates of cells. The vector name indicates the promoter and the transgene inserted between AAV ITRs. The second column indicates the rAAV size (ITR to ITR); the third, the rep-cap construct used for the production and the fourth whether adenovirus (wtAd5 or Ad.dts) or an adenoviral plasmid (pAdc) was used. The rAAV titer was measured by: [1] dot blot, [2] RCA. Contaminations[3] with adenovirus and rep-positive AAV particles were also measured by RCA. The last column indicates the final volume of virus after CsCl gradient purification and dialysis. rAAV stocks listed below the darker line in the middle of the table were purified following the centrifugation conditions described in Materials and Methods. Those listed above were purified following the protocol described by Snyder et al (1996). p./ml: particles/ml; i.p./ml: infectious particles/ml.

TABLE 2. Evaluation of different rep-cap expression plasmids for rAAV production. rAAV was produced from two 15-cm plates of 293 cells transfected with the AAVC-MVnlsLacZ vector, the adenoviral plasmid pAdc and the indicated rep-cap construct. Cells were collected three days after transfection and cell extracts purified as described in Materials and Methods. Each stock was tittered by: [1] dot blot, [2] RCA and [3] by an LFU assay performed on HeLa cells. The final volume of virus was of 7 ml for each stock.

TABLE 3. Comparison of the two adenoviral plasmids pAdc and pAdΔ for rAAV production. rAAV was produced from two 15-cm plates of 293 cells transfected with the pspRC construct, the AAVCMVnlsLacZ vector and the indicated adenoviral plasmid. Cells were collected 72, 96 and 120 hours after transfection and cell extracts purified as described in Materials and Methods. Each stock was tittered by: [1] dot blot and [2] RCA.

TABLE 4. Measure of infectious and transducing rAAVC-MVnlsLacZ particles produced using either Ad.dl324 (vAd) or an adenoviral plasmid (pAdc). Rep-cap functions were provided by the pspRC construct. In the case of the stock obtained with vAd, the virus was produced from 20 15-cm plates of 293 cells and the final volume was of 6.8 ml. In the case of the stock obtained with pAdc, the virus was produced from 50 15-cm plates of 293 cells and the final volume was of 13.4 ml. Recombinant AAV was tittered by: [1] dot blot, [2] RCA, [3] and [4] LFU assay on HeLa cells in the presence or in the absence of wtAd 5. ND, not done.

BRIEF DESCRIPTION OF THE FIGURES

FIG. 8 (Parts A–B): Schematic representation of the RES element. The RES element represented corresponds to nucleotides 190–540 of wild-type AAV genome (AF043303) (SEQ ID NO: 8). RBE (8A). FIG. 8B gives the nucleic acid sequence of this RES element (SEQ ID NO: 9).

MATERIALS AND METHODS

1. Cell Lines and Viruses 293 and HeLa cell lines were maintained in DMEM medium (SIGMA) supplemented with 10% heat-inactivated foetal calf serum (FCS, SIGMA) and 1% (vol/vol) penicillin/streptomycin (GIBCO BRL, 5000 U/ml).

Adenoviruses used are: wild type Adenovirus type 5 (wtAd5) (ATCC VR-5), Ad.dl324 (a gift from Transgène, France) and the double thermosensitive Ad.dts (Moullier P., unpublished data) which cumulates the ts125 mutation in the E2a region and the ts149 mutation located in the E2b DNA polymerase (Ginsberg et al., 1977). All these adenoviruses were produced and tittered on 293 cells using the standard procedures (Graham and Prevec, 1991).

Cells and adenoviruses were tested for the absence of wild type AAV (wtAAV) by PCR as indicated below.

Figure 1:
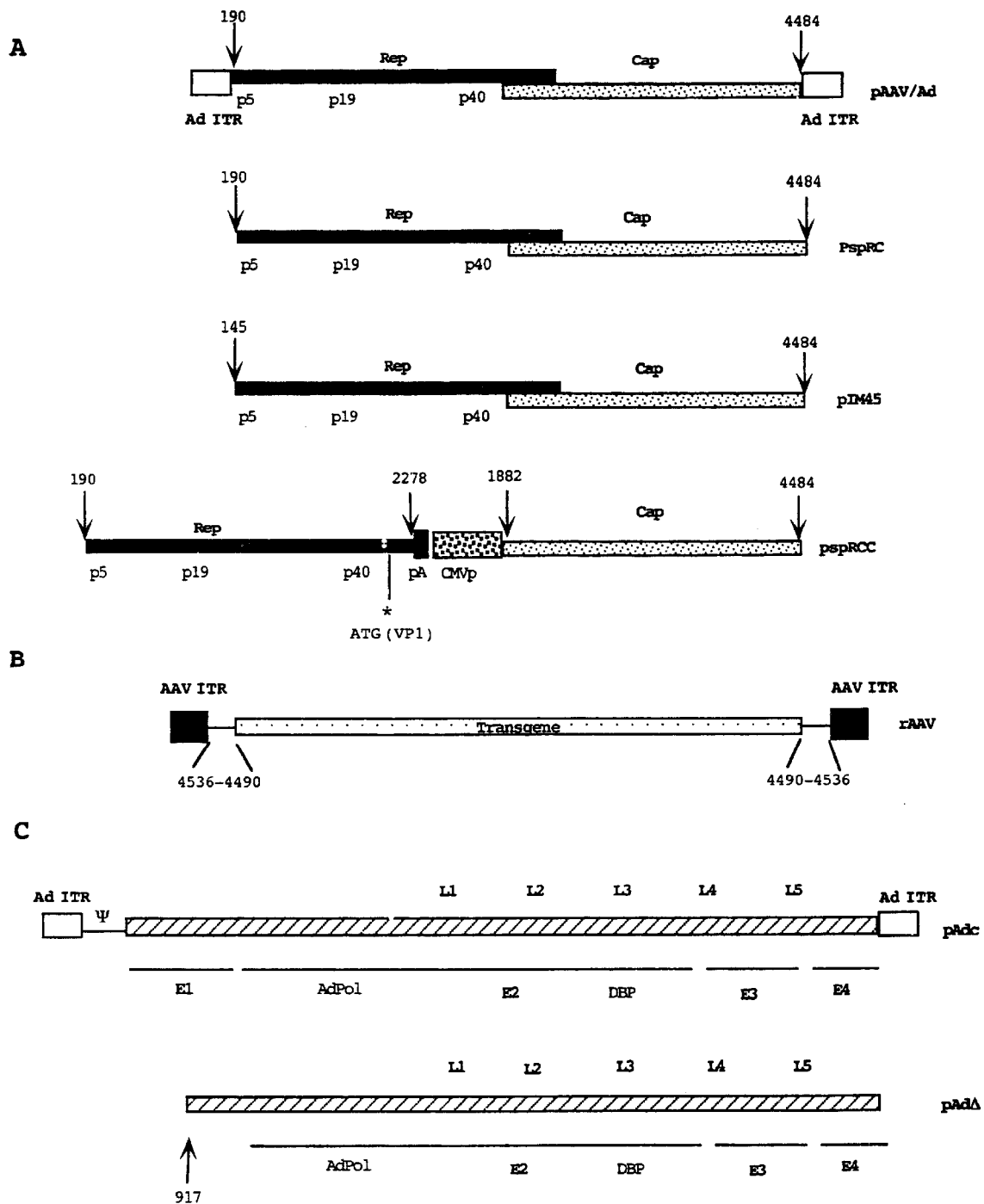
FIG. 1 (Parts A–C): Constructs used for rAAV production. A. Rep-cap constructs. Constructs pAAV/Ad and pIM45 are described in references (Samulski et al, 1989) and (Pereira et al., 1997) respectively. The pspRC and the RepCMVCap constructs are described in Materials and Methods. Numbers on the top correspond to position on the wild type AAV genome. CMVp: CMV promoter, pA: poly A signal from the bovine growth hormone gene. B. rAAV plasmids derived from the psub201 plasmid (Samulski et al., 1989). Numbers refer to wild type AAV sequences maintained in this plasmid and flanking the viral ITRs. C. Adenoviral plasmids: pAdc has the entire wild type Ad5 genome. Plasmid pAdΔ has a deletion of the 5' and 3' ITRs, the Ψ and E1 regions until position 917 of wtAd5.

HeLaRC32 cells are HeLa cells containing a rep-cap construct stably integrated into their genome. These cells were constructed as follows:

A stable cell line harboring the rep and cap genes was obtained by co-transfecting HeLa cells by the calcium-phosphate precipitation method with two plasmids:

- plasmid PGK-Neo which harbors the neomycin resistance gene under the control of the mouse phosphoglycerate kinase-1 promoter;
- plasmid pspRC which harbors the ITR-deleted AAV genome (from position 190 to 4492 bp of the wild-type AAV genome) inserted in the Psp72 plasmid (FIG. 1).

Clones isolated following G418 selection (1 mg/ml for three weeks) were screened for the presence of stably integrated rep-cap copies by Southern blot using a rep probe. Only four among 45 HeLa cell clones were positive by Southern blot analysis. Clone HeLaRC32 had the highest copy number per cell genome.

To document Rep and Cap protein expression, the HeLaRC32 cells were infected with wild-type adenovirus and analyzed by immunofluorescence using an anti-rep 78/52 monoclonal antibody and an anti-cap serum. About 50% of the cells were positive for cap proteins. Most of the cap positive cells (70%) also stained positive for Rep 78/52. These results indicated the presence of Rep and Cap proteins upon adenovirus infection of HeLaRC32 cells.

The production of functional Rep proteins by the HeLaRC32 cells was also tested by looking at their ability to replicate an AAV vector (ITR-transgene-ITR). For this, the cells were transfected with the rAAV-CMV-LacZ vector plasmid and subsequently infected with wild type adenovirus. Two days later, low molecular weight DNA was extracted following the Hirt procedure, digested with Dpnl, and analyzed by Southern blot using a LacZ probe. The result indicated the presence of the typical AAV replicative forms (the monomer and the dimer double-stranded DNA) upon adenovirus infection of HeLaRC32 cells, whereas no signal was seen when cells were uninfected or when they were not transfected with the AAVCMV-LacZ vector plasmid.

These results showed that cells prepared following the above protocols, especially starting with HeLa cells, stably produce functional Re and Cap proteins. HeLaRC32 cells have been used in the experimental section.

2. DNA Constructs 2.1. Rep-cap plasmids:

the pspRC plasmid (FIG. 1A) contains the ITR-deleted AAV genome (positions 190 to 4484 bp). It was excised as an XbaI fragment from the psub201 plasmid (Samulski et al., 1989) and inserted into the XbaI site of pSP72 plasmid (Promega).

The pspRCC plasmid (FIG. 1A) contains the rep gene (190 to 2278 bp of wt AAV) followed by the bovine growth hormone gene polyA signal and by the CMV promoter leading the expression of the cap ORF (1882 to 4484 bp of wt AAV). This plasmid was derived from pspRC by partially deleting the Cap ORF with XhoI which cuts at position 2232 of wtAAV (upstream of the stop signal for Rep 68 and Rep40) and further downstream in the plasmid backbone. The 324 bp polyA signal from the bovine growth hormone gene was then inserted downstream of the rep ORF to give the pspRep/pA plasmid. This construct codes for Rep 78 and Rep 52 proteins and contains the p40 promoter of AAV. In order to complete the Rep ORF, a 90 bp PCR fragment including region 2193 to 2278 bp of wtAAV was obtained using the following primers: 5'atgatttaaatcaggttgggctgccg3' (SEQ ID NO: 4; positions 2187 to 2212 of wtAAV) and 5'gctctagatgagcttccaccactgtc3' (SEQ ID NO: 5; positions 2278 to 2251 of wtAAV). This PCR fragment which includes a mutated VP1 start site (underlined in the primer sequence) was inserted between the SwaI and XbaI sites of the pspRep/pA plasmid to give plasmid pspRep/pA ΔVP1. To obtain plasmid pspRCC, a cassette composed of the cap ORF (1882 to 44874 bp of wtAAV) placed under the control of the CMV promoter (873 bp) was inserted downstream the poly signal of pspRep/pA (ΔVP1) at the unique PvuII site.

2.2. rAAV Vector Plasmids rAAV vector plasmids were derived from psub201 (Samulski et al., 1989) by deleting the rep-cap XbaI or SnaBI region and replacing it with different expression cassettes (FIG. 1B).

2.3. Adenoviral Plasmids

Two adenoviral plasmids were generated (FIG. 1C): i) plasmid pAdc contains the complete adenoviral genome cloned into the SuperCos plasmid (Stratagene); ii) the pAdΔ plasmid contains an adenoviral genome with both ITRs, the packaging signal (Ψ) and the E1 region deleted, also cloned into the SuperCos plasmid (Champion-Arnaud et al., manuscript in preparation).

Figure 2:
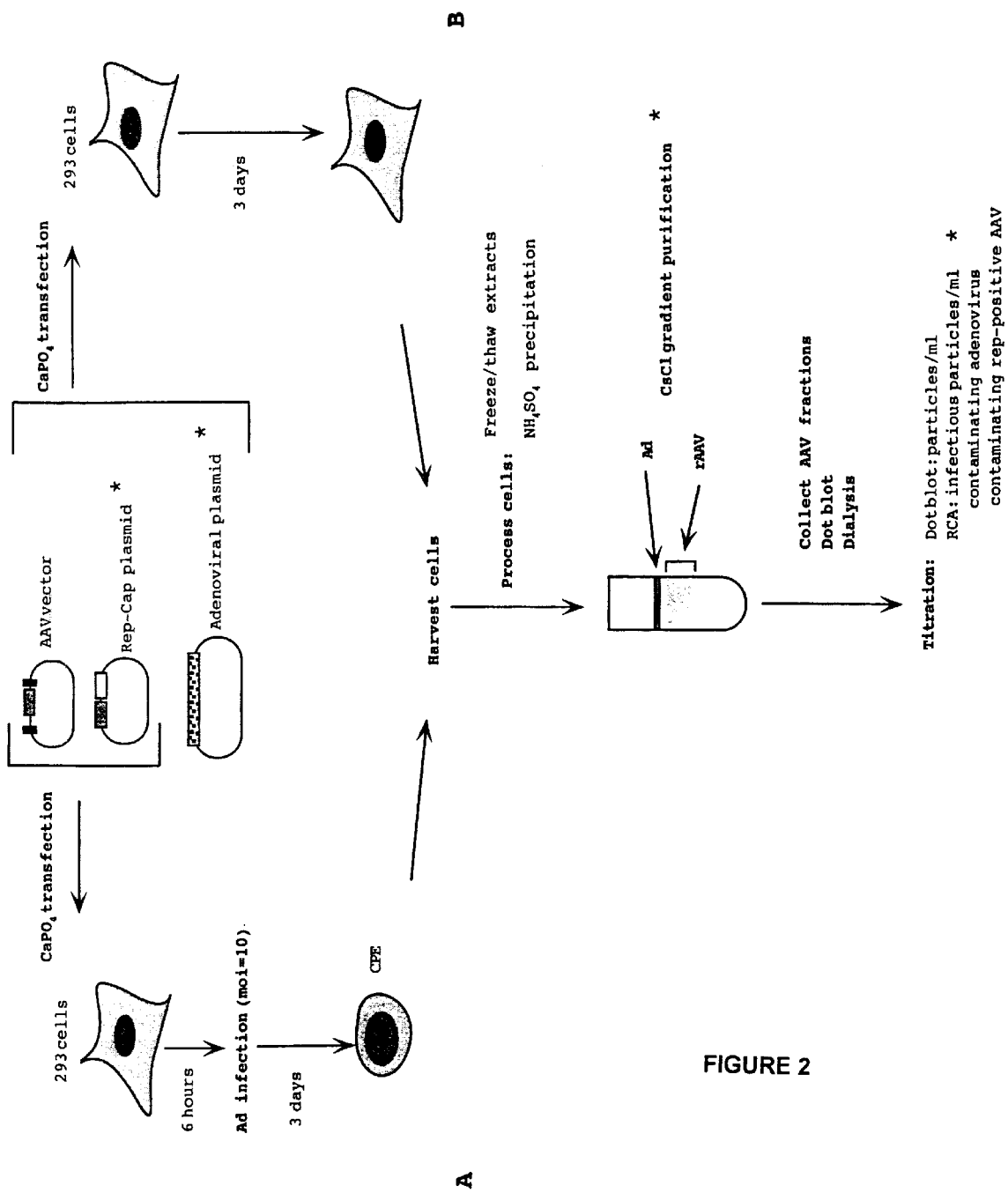
FIG. 2 (Parts A–B): rAAV production protocol. rAAV was produced using two different protocols: A. 293 cells were transfected with the rAAV vector and the rep-cap plasmid (1:1 ratio) and infected 6 hours later with adenovirus. When a cytopathic effect (CPE) was evident, cells were harvested and processed as described in Materials and Methods. B. 293 cells were transfected with the rAAV vector, the rep-cap plasmid and the adenoviral plasmid (1:1:2 ratio), washed after 6 hours, collected three days later and processed. After centrifugation rAAV containing fraction were pooled, dialyzed and tittered by dot blot and RCA as described in Materials and Methods. Asterisks indicate the steps which were modified from the original protocol (Snyder et al., 1996).

3. rAAV Production rAAV is produced using the procedure detailed in FIG. 2: on day 1, twenty five 15-cm plates of 293 cells (at approximately 80% of confluence) are co-transfected by the calcium phosphate method with the rep-cap and the vector plasmids (12.5 μg each). Six hours later, cells are washed with DMEM and infected with adenovirus (moi of 10) in DMEM 5% FCS (FIG. 2A). Under these conditions, a cytopathic effect (CPE) is visible approximately 3 days later. When using the Ad.dts adenovirus, the cells are incubated at 32° C. which is the permissive temperature for adenoviral growth. Alternatively, when rAAV is produced using an adenoviral plasmid (FIG. 2B), each dish is transfected on Day 1 with three plasmids: the rep-cap, the vector (12.5 μg each) and the pAdc or pAdΔ plasmids (25 μg). Six hours later, cells are washed and incubated in DMEM 5% FCS. No cytopathic effect is evident under these conditions and cells are usually harvested 3 days later unless otherwise indicated.

4. rAAV Purification

To purify rAAV particles, cellular pellets (each corresponding to six 15-cm plates) are resuspended in 20 ml of 10 mM Hepes pH 7.6/150 mM NaCl buffer and lysed by three cycles of freeze/thawing (dry ice with ethanol/37° C. water bath). The cell lysate is then centrifuged at 3000 rpm for 15 mn to remove cellular debris and further clarified by centrifuging at 10000 g (Beckman rotor JA17) for 10 mn at 4° C. The supernatant is then precipitated by addition of the same volume of cold saturated $(NH_4)_2SO_4$ (pH 7.0) and incubation for 20 mn on ice. After centrifugation at 12000 g for 20 mn at 4° C. (Beckman rotor JA17), the supernatant is removed and the pellet is resuspended in 3 ml of Phosphate Buffered Saline pH 7.0 (PBS) which are then loaded on top of a CsCl step gradient composed of 3 ml of 1.5 g/ml and 3 ml of 1.35 CsCl in PBS (Beckman Optiseal™ centrifuge tubes). The gradients are centrifuged for 6 hours (minimum time required to reach equilibrium) to overnight at 67000 rpm at 15° C. (Beckman rotor 90Ti). After centrifugation, an adenoviral band is visible in the middle of the tube, whichever adenoviral helper system was used (virus or plasmid). Ten fractions (20 drops each) are recovered from the bottom of the tube using the Beckman Fraction Recovery System and analyzed by dot blot to identify those containing rAAV genomes (see below). Usually, rAAV particles are concentrated within 6 fractions located below the adenoviral band. The rAAV containing fractions are then pooled and dialyzed for 24 hours against three changes of PBS supplemented with 0.9 mM $CaCl_2$ and 0.5 mM $MgCl_2$. The viral suspension is then aliquoted and stored at −80° C. without adding any stabilizer. The final titer of the rAAV preparation is determined using a frozen aliquot of virus following the methods described below.

An alternative purification method comprises chromatographic treatment of the rAAV preparation. In a typical experiment, the rAAV particles are collected on an iodixanol gradient or a "streamline" system (Pharmacia). When a iodixanol gradient is used, the pool of rAAV is first loaded onto an exclusion column (G25) to eliminate the iodixanol. The running buffer consists of Tris 10 mM, NaCl 80 mM, $Ca^{++}$ 1 mM and $Mg^{++}$ 1 mM.

The rAAV fractions, detected by dot blot, are pooled and loaded onto an anionic exchange column (Resource Q, Amersham Pharmacia Biotech). Flow rates vary between 1 ml/mn to 10 ml/mn. The setting allows low and medium pressure liquid chromatography. The loading buffer is made of Tris 10 mM, pH 8.0–8.5, NaCl 80 mM, $Ca^{++}$ 1 mM and $Mg^{++}$ 1 mM. Once loaded, elution of the rAAV particles is obtained using the elution buffer: Tris 10 mM, pH 8.0–8.5, NaCl 160 mM, $Ca^{++}$ 1 mM and $Mg^{++}$ 1 mM.

For this anionic exchange chromatography, a 1 ml capacity column is used to load an equivalent of $1 \times 10^8$ to $1 \times 10^9$ infectious particles total of rAAV. A 6 ml capacity column is used to load approximately $1 \times 10^{10}$ infectious particles at once. Higher viral loads can be treated for instance by fractionating the initial viral load.

The rAAV fractions eluting between NaCl 100 to 160 mM are pooled. The pooled rAAV are then loaded onto a Sephacryl (S500) column to exclude the viral particles and separate them out of residual protein and lipid contaminants.

5. Titration of rAAV Stocks

Two different methods are used to measure the rAAV titer: 1) the dot blot analysis to measure the number of particles/ml based on the quantification of viral DNA; 2) a modified Replication Center Assay (RCA) to measure the number of infectious particles/ml, as well as the level of contaminating adenovirus and rep-positive AAV.

5.1. Dot Blot Analysis 1 and 10 μl of the viral stock are incubated with 20 U of DNaseI (Boehringer Manheim) in 200 μl of DMEM for 1 hr at 37° C. Two hundred μl of 2×Proteinase K solution (20 mM Tris-HCl pH 8.0, 20 mM EDTA pH 8.0, 1% SDS) are then added and the samples incubated further for 1 hr at 37° C. Viral nucleic acid are then purified by a phenol/chloroform extraction, precipitated after addition of NaOAc/ethanol and incubation for 20 mn at −80° C. After 30 mn of centrifugation at 15000 g, the nucleic acid pellet is washed in 75% ethanol and resuspended in 400 μl of 0.4M NaOH, 10 mM EDTA. After heating at 100° C. for 5 mn, the DNA is loaded on a Zetaprobe membrane (Biorad) using a dot blot apparatus. As a standard for the determination of the amount of viral DNA, several dilutions of rAAV vector plasmid used to produce the virus are loaded on the same membrane. After blotting, the membrane is prehybridized for 30 mn at 60° C. A denatured fluorescein-labelled probe (Amersham, Gene Images random prime labeling module) corresponding to the cDNA included in the rAAV vector is then added and incubated overnight at 60° C. The following day the membrane is processed according to the manufacturer's protocol (Amersham, Gene Images CDP-star detection module) and exposed to an autoradiography film.

5.2. Modified RCA

HeLaRC32 (a stable HeLa cell clone expressing rep-cap) and control HeLa cells are seeded the previous day in a 48-well plate ($8 \times 10^4$ cells/well), in DMEM containing 10% fetal calf serum (FCS) (for each rAAV preparation: 3 wells with HelaRC32 for titration; 1 well with HelaRC32 to measure adenovirus contamination; 2 wells with HeLa to measure rep-positive AAV contamination).

The following day, cells are infected, as appropriate, with the rAAV samples and with or without helper adenovirus.

In this regard, the stocks of adenoviruses are prepared as follows, generally under P3 confinement conditions. The helper virus used in these experiments is a wild-type adenovirus type 5 (Adwt5) at a Multiplicity of Infection (MOI) of about 500. A mix containing the number of pfu necessary to infect all the wells into the appropriate volume of medium (DMEM, 5% FCS) is prepared. For adenovirus infection, the medium is removed from the cells and 200 μl of the solution (DMEM, 5% FCS) containing the adenovirus at the selected MOI are added.

For rAAV titration, three wells of HelaRC32 cells, infected with adenoviruses as described above, are infected with 3 dilutions of the rAAV preparation ($10^{-4}$, $10^{-5}$ and $10^{-6}$) prepared by serial dilution in DMEM, 5% FCS (10 μl of the rAAV preparation into 90 μl of medium). 2 μl of each rAAV sample are added to the 200 μl of medium with adenovirus.

For measuring adenovirus contamination, one well of HelaRC32 cells, not infected with adenoviruses, is infected with the rAAV preparation (pure sample). 2 μl of each rAAV sample are therefore added to the 200 μl of medium without adenovirus.

For measuring rep-positive AAV contamination, two wells of HeLa cells, infected with adenoviruses as described above, are infected with samples of the rAAV preparation (pure sample and $10^{-1}$ dilution in DMEM, 5% FCS). 2 μl of each rAAV sample are added to the 200 μl of medium with adenovirus.

Twenty four hrs later, the medium is removed from each well, and the wells are washed twice in PBS. The cells are trypsinized by addition of 200 μl trypsin for 10 minutes at 37° C. 300 μl DMEM, 5% FCS are added and the cells are detached, by pipetting up and down several times. The cell suspension is then added to an eppendorf tube. The wells are washed again with 500 μl of PBS and this volume is added to the cell suspension. The eppendorf tubes are centrifuged (3000 rpm, 5 minutes), and the supernatant is removed with a pipet. The cell pellets are suspended in 1 ml PBS by pipetting up and down several times, and stored on ice.

Each suspension is filtered under vacuum through a Zeta-probe membrane (Biorad). The filters are put on a Whatman paper soaked in 0.5 M NaOH/1.5 M NaCl for 5 mn, and then neutralized in a 1 M Tris HCl (pH 7.5)/2×SSC (0.3 M NaCl, 0.03 sodium citrate) solution. Filters are dried on dry Whatman paper and hybridized overnight to a fluorescein-labelled probe corresponding to the cDNA included in the rAAV vector (Amersham, Gene Images random prime labeling module). The filters are then processed as described by the manufacturer (Amersham, Gene Images CDP-Star detection module).

6. LacZ Forming Unit (LFU) Assay

To measure the transducing activity of rAAV harboring the β-galactosidase gene (LacZ), HeLa cells, seeded the day before at $2 \times 10^5$ cells per well (24-well plate), were infected with pure or diluted rAAV in DMEM 5% FCS in the presence or in the absence of wtAd5 (m.o.i. of 50). Twenty-four hours later cells are washed in PBS, fixed with 0.5% glutaraldehyde for 5 mn at room temperature and then stained with 5-bromo-4-chloro-3-indolyl-β-D-galactopyranoside (X-Gal) for 6 hrs at 37° C.

7. Southern Blots on Low Molecular Weight DNA

For extracting low molecular weight DNA, cells are trypsinized and lysed in a solution of 10 mM TrisHCl (pH 8.0)/10 mM EDTA/1% SDS for 30 mn at 37° C. After addition of Proteinase K at 500 μg/ml final (Boehringer Manheim), the lysate is incubated for 2 hrs at 37° C. To precipitate high molecular weight DNA, 5 M NaCl is added to the cell lysate (final concentration of 1.1 M) and incubated overnight at 4° C. High molecular weight DNA is pelleted by centrifugation at 10000 RPM for 20 min at 4° C. and the supernatant is extracted twice with chloroform at room temperature. The nucleic acids are then precipitated with ethanol and resuspended in 10 mM Tris pH 8.0/1 mM EDTA containing 200 μg/ml of RNase (Boehringer Manheim). After incubation for 15 mn at room temperature, the DNA is extracted twice with chloroform and ethanol/NaOAc precipitated. The final pellet is resuspended in 10 mM Tris pH 8.0/1 mM EDTA and stored at −20° C. For analysis, the DNA is digested with DpnI (which cleaves only input methylated plasmid DNA), run on a 1% agarose gel and transferred under alkaline conditions on a Hybond $N^+$ membrane (Amersham). The membrane is hybridized to a fluorescein-labelled probe and processed as described above.

8. Detection of Rep Sequences by PCR

Cells and adenoviral stocks were routinely assayed for the presence of rep-positive AAV by PCR. The PCR primers were: Rep1 (5'-TATTTAAGCCCGAGTGAGCA-3'; SEQ ID NO: 6) which corresponds to positions 255 to 275 of wild type AAV in the p5 promoter; and Rep3 (5'-AAAGTTCTCATTGGTCCAGT-3'; SEQ ID NO: 7) which corresponds to positions 1417 to 1397 of wild type AAV in the Rep52/40 ORF. PCR was carried using Taq polymerase (Gibco BRL) for 25 cycles (30 sec. at 94° C., 30 sec. at 55° C., 33 sec. at 72° C.) in a Perkin Elmer thermocycler (Gene Amp PCR System 9600).

Results rAAV was initially produced following the protocol described by Snyder et al. (1996). Briefly, twenty five 15-cm plates of 293 cells are transfected with two plasmids: one harboring the rep and cap genes and the other the rAAV vector (FIG. 2A). Six hours after transfection, cells are infected with adenovirus (wild type, or Ad.dts). When a cytopathic effect appeared, cells were harvested, lysed and extracts were purified through two cesium chloride gradients. A first technical change was introduced in the purification step on the CsCl gradient, reducing the centrifugation time down to six hours to reach equilibrium. This modification did not affect the rAAV yields but instead increased the final volume of virus. Furthermore, beside this technical improvement, several additional major modifications were introduced in the rAAV production procedure (FIG. 2): the first one concerns the titration method employed to measure the number of infectious particles produced; the second one is related to the use of different rep-cap expression constructs; the third modification concerns the use of an adenoviral plasmid instead of an adenoviral particle to provide helper functions needed for rAAV replication and assembly; the fourth modification relates to the discovery of RES sequence and their introduction into rAAV vectors to increase the efficiency of the method. Another preferred characteristic of the present invention relates to the use of stable rep-cap cell lines to provide the AAV transcomplementing functions and thus, eliminate the need for a rep-cap plasmid.

A summary of the 18 large scale rAAV stocks produced is presented in Table 1. A detailed analysis of these results is presented below.

Figure 3:
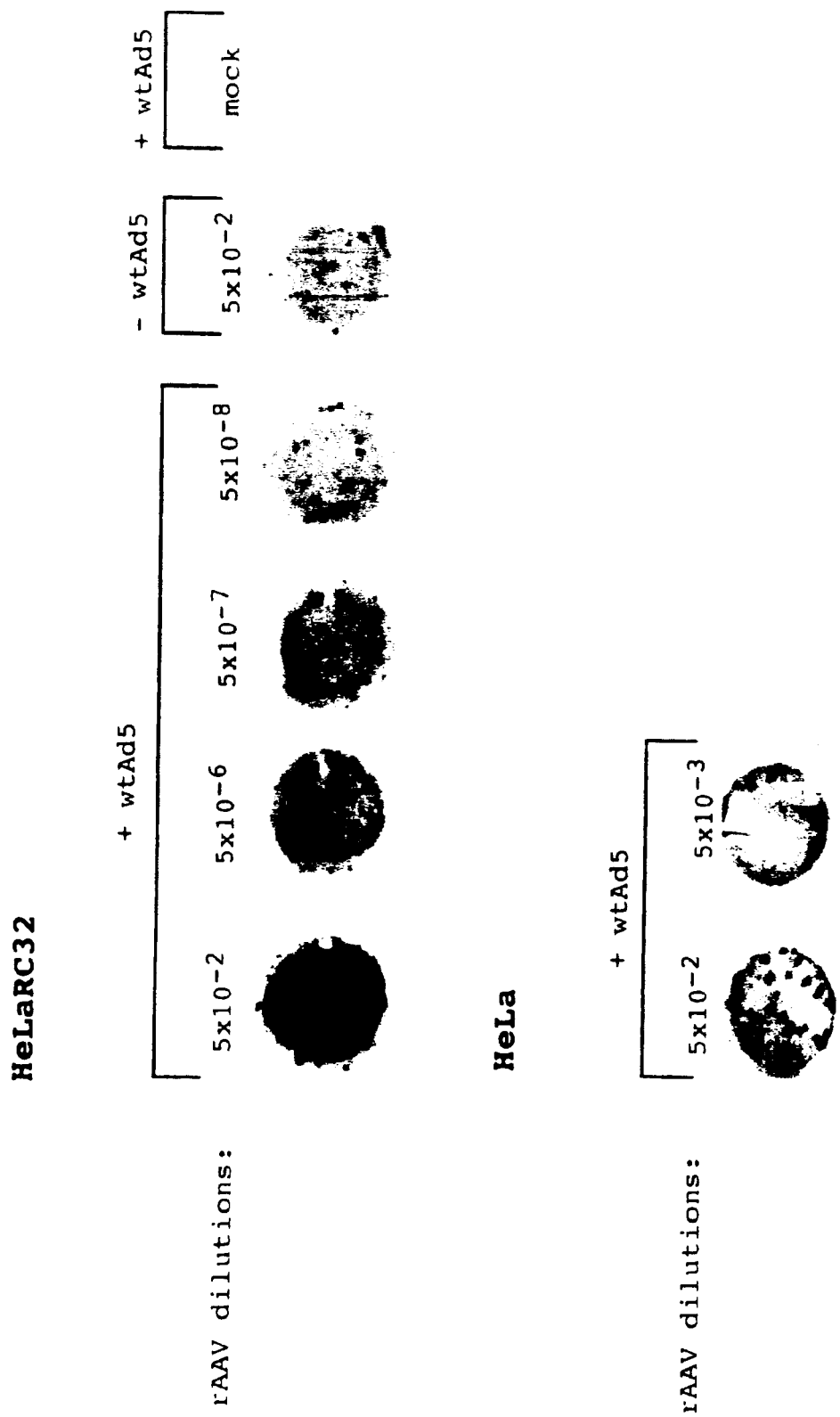
FIG. 3: Characterization of rAAV by a modified Replication Center Assay (RCA). HeLaRC32 cells, harboring two integrated copies of an ITR-deleted AAV genome or control HeLa cells were infected with different dilutions of the rAAV stocks and either infected or not with wtAd5 (see Materials and Methods for details). Twenty-four hours later cells are trypsinized, filtered through a membrane, lysed and the filters were hybridized overnight with a transgene probe. The number of infectious rAAV particles is determined by counting the number of spots on HeLa32RC cells in the presence of adenovirus. The same assay performed in the absence of adenovirus gives the level of contamination with infectious adenoviral particles. No signal is detected when HeLaRC32 cells are infected with adenovirus alone. Finally, the result on control HeLa cells in the presence of adenovirus gives the level of contamination with rep-positive AAV.

1. Use of a Stable Rep-cap HeLa Cell Clone for Titration and Characterization of rAAV Stocks Quantification of viral DNA by dot blot is generally used to measure the amount of rAAV particles. This assay however, does not provide any information about the number of infectious rAAV particles which relies either on the detection of the rAAV transducing activity or in the measure of infectious particles in a Replication Center Assay (RCA). This latter method is particularly interesting since it does not depend upon the expression of the transgene but only upon the ability of rAAV to infect a target cell (generally 293 cells) and to replicate its genome in the presence of adenovirus and Rep proteins. In the originally described RCA (McLaughlin et al., 1988; Yakobson et al., 1987), Rep proteins are provided by adding wtAAV which requires a restricted area in order to prevent any contamination. Our rationale was to circumvent the use of wtAAV in this assay by developing a stable cell clone expressing Rep proteins. A stable HeLa cell clone with two integrated copies of an ITR-deleted AAV genome (HeLaRC32 cells) was thus generated. In the modified RCA, HeLaRC32 or control HeLa cells are infected with different dilutions of rAAV in the presence or in the absence of wild type adenovirus, and individually analyzed for the presence of replicating rAAV using a transgene probe. A typical result obtained using this assay is presented in FIG. 3 where the number of spots obtained with the HeLaRC32 cells infected with rAAV and adenovirus can be translated as the number of infectious rAAV particles; and the number of spots obtained with the HeLaRC32 cells infected with rAAV, but in the absence of adenovirus, represents the number of contaminating infectious adenoviral particles. As expected, no signal was detected when HeLaRC32 cells were infected with adenovirus alone. Finally, when control HeLa cells were infected with rAAV and adenovirus, some signal was always detected suggesting that rAAV was amplified in these cells (FIG. 3). A plausible interpretation of this result is that rAAV stocks are contaminated with rep-positive AAV particles. This last result was thus used to measure the number of rep-positive AAV particles in all the large scale rAAV stocks. The development of this modified RCA allowed us to fully characterize the effect of each modification introduced in the rAAV production protocol as described below.

2. Evaluation of Different Rep-cap Expressing Plasmids for rAAV Production

The pAAV/Ad plasmid, described in the standard rAAV production method (Samulski et al., 1989), harbors the AAV rep-cap sequences flanked by the adenovirus ITRs (FIG. 1A). After producing three rAAV stocks with the pAAV/Ad plasmid, the following rAAV stocks were produced using the pspRC construct which harbors only the rep-cap sequences in a psp72 backbone (FIG. 1A). The use of the pspRC plasmid for large scale rAAV production did not affect the total number of physical particles recovered, which ranged between $10^{11}$ and $5\times10^{12}$ total particles, but instead increased the infectious particles yields, as measured by RCA (Table 1 and FIG. 4). Indeed, particles to infectious particles ratios ranged between $10^3$ and $10^4$ when the pAAV/Ad was the trans-complementing plasmid, whereas, rAAV stocks produced with the pspRC plasmid consistently showed a ratio below 50 and this independently of the adenoviral helper functions provided (adenoviral virions or adenoviral plasmid).

Other rep-cap constructs were further tested on small scale rAAV productions performed on two 15-cm plates of 293 cells. The pspRC plasmid was compared to two other constructs: i) plasmid pIM45 (Pereira et al, 1997) which harbors approximately the same rep-cap region extended on the 5' end of 45 bp from wtAAV (FIG. 1A); ii) plasmid pspRCC which harbors the rep ORF under the control of the native AAV promoters followed by the cap ORF under the transcriptional control of the CMV promoter (FIG. 1A). This last construct was used to test whether expression of the cap gene under the control of a strong heterologous promoter can increase the viral titer as recently reported (Vincent et al., 1997). rAAV produced on small scale experiments was purified on a CsCl gradient and characterized by dot blot, RCA and by a LacZ Forming Unit assay (LFU) on HeLa cells. As indicated in Table 2, approximately the same number of particles was measured by dot blot. Similarly, the number of infectious or transducing particles was not significantly affected by the rep-cap plasmid used.

3. Use of an Adenoviral Plasmid for rAAV Production

Recombinant AAV stocks were initially produced using either wtAd5 or Ad.dts adenovirus. None of these virions did actually make any difference in terms of rAAV production (Table 1). Subsequently, we tested whether adenoviral virions could be replaced by plasmid pAdc harboring the complete adenoviral genome from wtAd5 (FIG. 1C). The production protocol, thus, consisted in an initial transfection of three plasmids (FIG. 2B): the rAAV vector plasmid, the rep-cap plasmid and the adenoviral plasmid (1:1:2 ratio). No cytopathic effect was observed even five days after transfection. Consequently, to purify rAAV, cells were usually scraped from the plates three days after transfection and processed as previously described.

Figure 4:
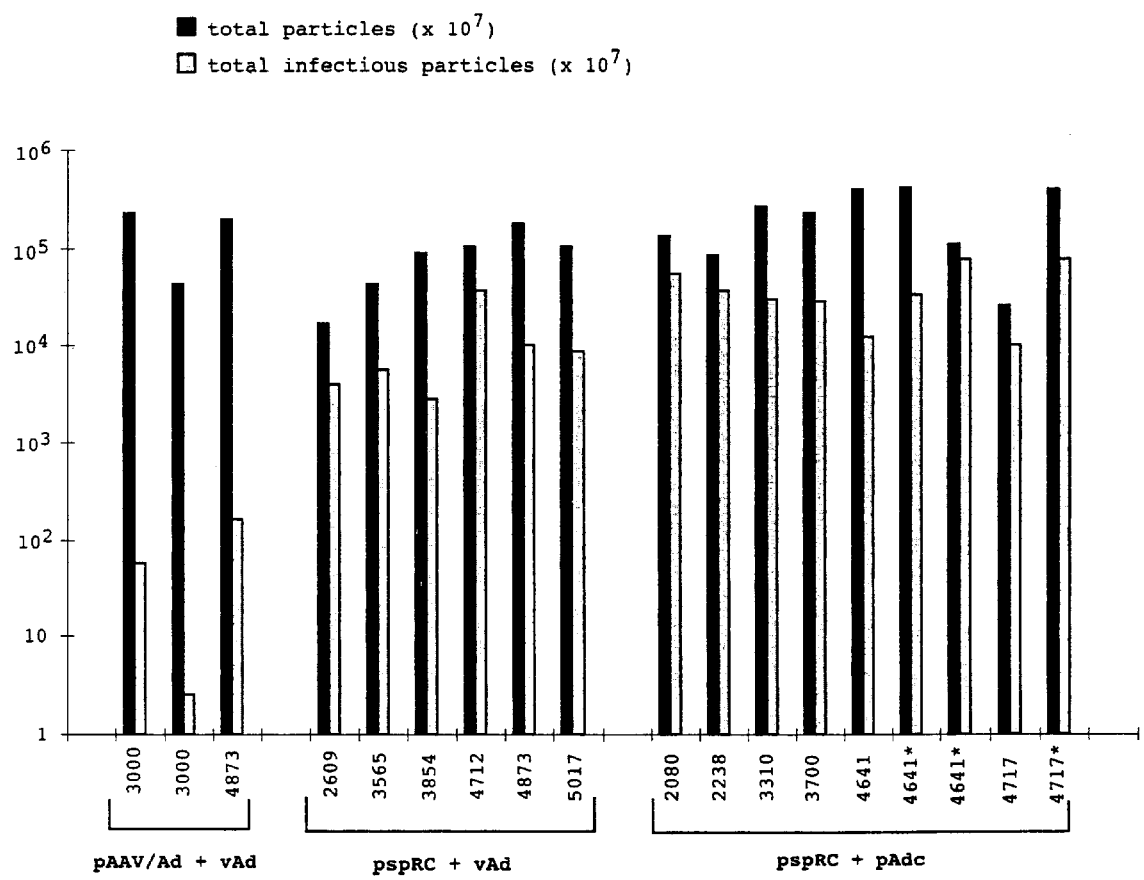
FIG. 4: Comparison of rAAV yields produced with different rep-cap plasmids and either adenovirus or an adenoviral plasmid. rAAV stocks described in Table 1 were tittered by dot blot and RCA to measure, respectively, the number of particles and infectious particles. The x axis indicates the size of each rAAV and the production protocol followed: pAAV/Ad+vAd. transfection of the rAAV vector with the pAAV/Ad plasmid followed by infection with adenovirus; pspRC+vAd. transfection of the rAAV vector with the pspRC plasmid followed by infection with adenovirus; pspRC+pAdc. transfection of the rAAV vector, the pspRC construct and the adenoviral plasmid pAdc harboring the entire adenoviral genome. All the rAAV stocks were prepared from 25 15-cm plates of 293 except for stocks marked with an asterisk which were prepared from 50 15-cm plates of cells.

Titration of rAAV stocks, produced using this new procedure, indicated that replacement of adenoviral virions by the pAdc plasmid did not affect the particles yields which ranged between $10^{11}$ and $5\times10^{12}$ total particles (Table 1 and FIG. 4). Similarly, the infectious particles yields remained unchanged (FIG. 4), although some variability in the production yields using the pAdc plasmid was observed, essentially because of some variability in transfection efficiencies.

We next compared the pAdc plasmid with plasmid pAdΔ which harbors an adenoviral genome lacking the two ITRs, the packaging signal and the E1 region (FIG. 1C). Two 15-cm plates of 293 were transfected with the rAAV vector plasmid, the pspRC plasmid and either the pAdc or the pAdΔ constructs. To determine the optimal harvesting time for rAAV production, the cells were collected at 72, 96 and 120 hours post-transfection. Cellular extracts were purified on a CsCl gradient and the results of the dot blot and of the RCA are presented in Table 3. The same rAAV titer ranging between $10^{10}$ and $5\times10^{10}$ infectious particles/ml was obtained with both plasmids. Incubation of the cells for more than three days did not significantly affect the particles/ml titer, however, a slight reduction in the infectious particles yields was observed.

Both the pAdc and the pAdΔ adenoviral plasmids, generated a slight band observed at equilibrium in the CsCl gradients at a position similar to mature adenoviral particles. We were not able, however, to detect plaques after incubation of 293 cells with an aliquot of the band obtained with the pAdc plasmid. Furthermore, and more importantly, no adenoviral contamination was observed in most of the large scale rAAV stocks (7/9) produced using the pAdc plasmid as detected by RCA (Table 1). Also, the low level of adenoviral contamination (2.5 $10^3$ i.p./ml) observed in two rAAV stocks has not yet been confirmed by other methods.

4. Detection of Rep-positive AAV in the rAAV Stocks

Figure 5:
FIG. 5: Analysis of the replication of rAAVCMVnlsLacZ in 293 cells. 293 cells were infected with rAAVCM-VnlsLacZ (m.o.i. of 100 as defined by RCA), produced either with adenovirus (vAd) or the adenoviral plasmid (pAdc), in the presence or in the absence of Ad.dl324 (m.o.i. of 10). Three days later, cells were harvested, lysed, and low molecular weight DNA was extracted, run on a gel, transferred to a membrane and hybridized to a LacZ probe as described in Materials and Methods. ss DNA: single-stranded DNA; mRF: monomer double-stranded DNA; dRF: dimer double-stranded DNA.

The rAAV stocks were tested in a modified RCA for the presence of contaminating rep-positive AAV. Infection of control HeLa cells with different dilutions of rAAV and adenovirus resulted in the detection of some level of replicating rAAV (detected with a transgene probe) in all the rAAV stocks (FIG. 3). This suggested that some Rep activity had been transferred to these cells. This level of contamination ranged between $10^4$ and $5\times10^7$ infectious rep-positive AAV particles/ml and this independently of the use of adenovirus or of an adenoviral plasmid (Table 1). To substantiate this result, 293 cells were infected with rAAVCMVnlsLacZ, produced either with adenovirus or the pAdc plasmid, in the absence or in the presence of Ad.dl324 and low molecular weight DNA was analyzed on a Southern blot using a LacZ probe. As shown in FIG. 5, the typical AAV replicative forms were detected when cells were co-infected with adenovirus, whereas only input single stranded DNA was seen in cells infected with rAAVCM-VnlsLacZ alone. This result suggested that particles containing rep sequences and/or Rep proteins are present in the rAAV stocks. To check for the presence of rep sequences, DNA was extracted from 10 µl of a rAAV stock (approximately $10^9$ particles) and analyzed by PCR using primers located in the p5 promoter and the rep gene (see Materials and Methods). As expected, an amplification product was detected in all the rAAV stocks (data not shown). Altogether, these data suggest that some rep DNA is packaged during rAAV assembly in 293 cells. Furthermore, the results presented show that the use of a rep-cap plasmid devoid of adenoviral ITRs according to the present invention significantly reduces the contamination by $rep^+$ AAVs in the stocks obtained.

5. Identification, Cloning and Characterization of RES Sequences

This example discloses the discovery, cloning and characterization of non-ITR sequences which are implicated in cis in the encapsidation of the AAV genome into AAV capsids. This example also illustrates how these sequences can be used to package heterologous polynucleotides (free of functional AAV ITRs) into AAV capsids and to increase the yields of rAAV production methods.

5.1. Encapsidation of AAV Rep-cap Genome in the Absence of the Viral ITRs

Figure 7:
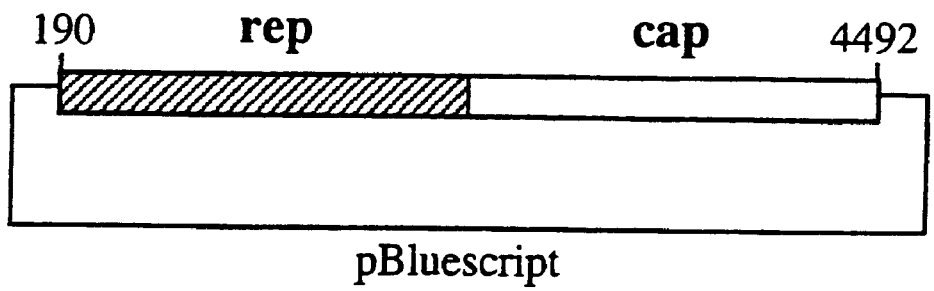
FIG. 7: Description of plasmids BS-RC, dITR-RC and dITR-RCΔ. Plasmid BS-RC comprises a rep-cap unit (nucleotides 190–4492) of AAV, inserted in the Bluescript plasmid. Plasmid dITR-RC comprises the same rep-cap unit as plasmid BS-RC, but flanked by the adenovirus type-5 ITRs, also inserted in the Bluescript plasmid. Plasmid dITR-RCΔ is identical to plasmid dITR-RC, with a deletion of 350 bp in the rep unit (nucleotides 190–540).
Figure 7:
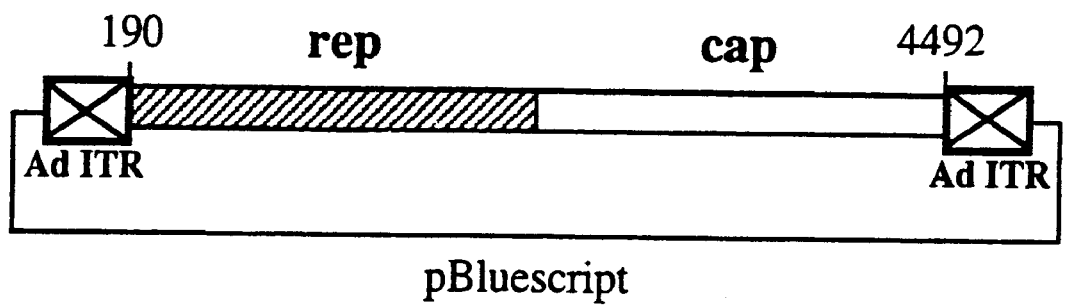
Figure 7:
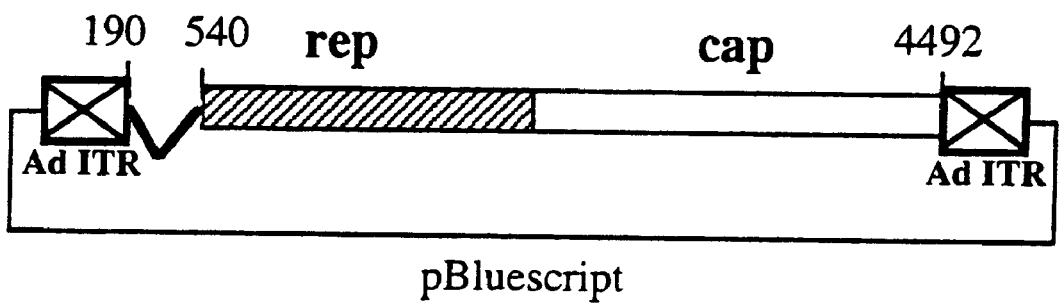

To demonstrate that a rep-cap genome can be packaged in the absence of the AAV ITRs, 293 cells were transfected with a plasmid harboring an ITR-deleted rep-cap genome associated with or without the adenovirus ITRs (FIG. 7, plasmids dITR-RC and BS-RC respectively). Cells were then infected with adenovirus, and AAV particles were purified on a CsCl gradient. After treatment of the particles with DNase I, the viral DNA packaged inside the particles was extracted and analyzed on a Southern blot using either a rep or an adenovirus ITR probe.

Using a rep probe, a hybridization signal was detected with viral DNA extracted from viral preparations produced using both plasmids (BS-RC or dITR-RC). However, a more intense signal was observed using the dITR-RC plasmid. The position and the pattern of this hybridization signal on the Southern blot was similar to that observed in the case of single-stranded viral DNA. This result indicated that a rep-cap genome can be found associated with AAV capsids in the absence of the AAV ITRs.

When the adenovirus ITR probe was used, a specific band migrating at the same position as that observed using a rep probe was observed only for the preparation made with the dITR.RC construct. This result indicates that in this case, the rep-cap genome found associated with AAV capsids also harbored the adenovirus ITRs.

Both these results indicate that a rep-cap genome can be packaged into AAV capsids despite the absence of the AAV ITRs, thus suggesting the presence of specific packaging signals in the rep-cap sequence.

5.2. Identification and Cloning of Viral Sequences Involved, in cis, in the Encapsidation of an ITR-deleted Rep-cap Genome To be packaged, the rep-cap genome has first to be replicated in order to generate single-stranded DNA which is the form encapsidated into AAV capsids. In the case of wild-type AAV, replication is initiated from the viral ITRs which harbor the binding element for Rep78/68 (RBE) and its nicking site (terminal resolution site or trs). Interestingly, a Rep binding element associated with a cryptic trs is present in the p5 promoter, approximately 50 bp downstream from the 5' ITR. Moreover, we discovered in this same region the presence of a putative palindromic structure upstream to the RBE and trs (FIG. 8). The respective position of these three elements (palindrome, RBE and TRs) is similar to that observed in the AAV ITR. These observations led us to concentrate on the role of these three elements of the p5 promoter in the encapsidation of an ITR-deleted rep-cap genome.

These three elements (palindrome, RBE and trs) were first deleted from the plasmid dITR-RC by removing a 350 bp region extending from the 5' end of the p5 promoter to the beginning of the rep coding region (nucleotides 190 to 540 of wtAAV). This new construct, named dITR.RCΔ (FIG. 7) was transfected into 293 cells which were subsequently infected with adenovirus. Because Rep proteins could not be produced by the dITR.RCΔ construct, they were supplied by co-transfection of the BS-RC plasmid which harbors the entire rep-cap coding region. The analysis of viral DNA packaged into AAV capsids was performed by Southern blot using an adenovirus ITR probe. Opposite to what was observed with the dITR.RC plasmid, no signal was detected using the dITR.RCΔ construct. These results indicated that the 350 bp deleted from the rep-cap genome contains essential elements for its replication and/or encapsidation in the absence of the AAV ITRs. This 350 bp region was named RES (Replication Encapsidation Sequence).

5.3. Use of RES to Package a Polynucleotide into AAV Capsids

The previous experiment demonstrated that the deletion of the RES element prevents the encapsidation of the rep-cap genome. We next investigated whether the RES element could confer to any heterologous sequence the ability to be packaged into AAV capsids.

Figure 9:
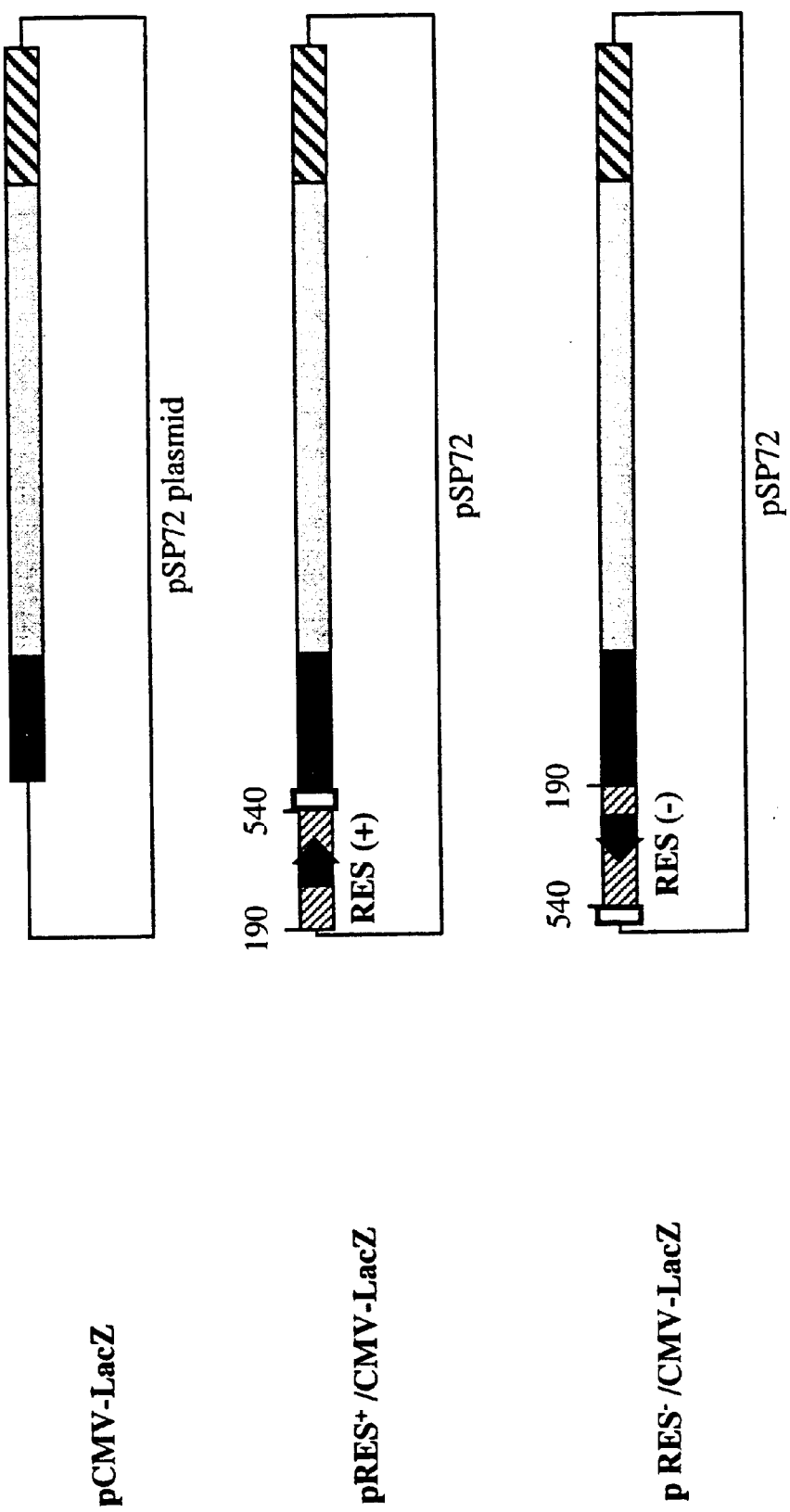
FIG. 9: Description of plasmids pCMV-LacZ, pRES+/CMV-LacZ and pRES−/CMV-LacZ. Grey box: LacZ gene linked to a nuclear localization signal; black box: Promoter and enhancer of the cytomegalovirus (CMV) (NdeI-BamHI fragment of the pRC/CMV plasmid); empty box: double strand oligonucleotide (20 bp) harboring a translation stop codon in each of the three opening reading frames; thick hatched box: polyadenylation signal of the bovine growth hormone (BamHI-PvuII fragment of the pRC/CMV plasmid); thin hatched box: RES element (nucleotides 190–540 of AAV).

Three constructs were made (FIG. 9):
  pCMV-LacZ, harboring only the LacZ expression cassette;
  pRES$^+$/CMV-LacZ, harboring the LacZ cassette and a RES element, in the sense orientation, inserted upstream of the CMV promoter;
  pRES$^-$/CMV-LacZ, harboring the LacZ cassette and a RES element, in the antisense orientation, inserted upstream of the CMV promoter.

To determine if any of these constructs could be packaged into AAV capsids, they were individually transfected into HeLaRC32 cells which have integrated into their genome a copy of the ITR-deleted AAV genome (see Materials and Methods). These cells, which provide Rep and Cap functions, were used to limit the recombination events between the plasmids harboring the RES elements and the rep-cap genome. After transfection, the cells were infected with adenovirus, and AAV particles were purified on a CsCl gradient. The DNA packaged into AAV capsids was analyzed on a Southern blot using a LacZ probe. The results obtained indicated the absence of a specific signal when cells were transfected with plasmid pCMV-LacZ. In contrast, a band hybridizing to the LacZ probe was specifically detected when cells were transfected with plasmid pRES$^+$/CMV-LacZ and pRES$^-$/CMV-LacZ. This result indicated that the RES element can confer to the CMV-LacZ sequence the ability to be packaged into AAV capsids.

To further confirm this observation, AAV particles obtained using each of the three plasmids (pCMV-LacZ, pRES$^+$/CMV-LacZ and pRES$^-$/CMV-LacZ) were used to infect HeLa cells in the presence of adenovirus. Twenty-four hours after infection, the cells were fixed and stained with X-Gal to detect cells expressing the LacZ gene. No blue cells were observed when using the pCMV-LacZ-derived viral preparations. In contrast blue cells were seen when using viral stocks produced using the pRES$^+$/CMV-LacZ and pRES$^-$/CMV-LacZ plasmids. This result indicated that infectious particles that could transfer the LacZ expression cassette were present in the preparations (30 LacZ-forming units total were obtained with each plasmid for $6 \times 10^7$ transfected cells). This observation further implies that the single-stranded DNA packaged into these particles had been converted into a transcriptionally active double-stranded form. In the case of wild-type AAV or of recombinant AAV, this event is primarily mediated by the presence of the AAV ITRs which, in their palindromic conformation, provide a 3'OH free end necessary to start the polymerization process. A similar mechanism might be mediated by the small palindrome in the RES+/CMV-LacZ and RES−/CMV-LacZ genomes. An alternative possibility would be that the double-stranded DNA form was generated by the annealing of two complementary single-stranded molecules as observed in cells infected with wtAAV.

In conclusion, our observations demonstrate that the RES element can confer to an heterologous sequence the ability to be packaged into AAV particles and that at least a portion of these particles are infectious.

5.4. Use of RES Sequences to Improve rAAV Yields

Since the RES sequence can mediate the replication and/or encapsidation of any nucleic acid into AAV particles, it can also be used to increase the packaging efficiency of rAAV vector plasmids (i.e., harboring AAV ITRs) and thus, to improve the yield of infectious recombinant AAV particles. For that purpose, one or several RES elements are inserted into an AAV vector (ITR-transgene-ITR) to analyze its effect in the context of the AAV ITRs. Indeed, it is expected that the RES element cooperates with the AAV ITRs to optimize the encapsidation of single-stranded DNA into AAV capsids. AAV particles comprising either a standard AAV vector (ITR-transgene-ITR) or a RES-containing vector (ITR-RES-transgene-ITR) are produced using adenovirus-infected HeLaRC32 cells. The yield of infectious particles produced using the two kinds of vector is measured and compared following standard procedures.

5.5. Constructions of RES Variants

This section illustrates the construction of RES elements having, for instance, reduced size, while retaining their packaging activity.

Deletions and point mutations of the RES element are introduced into the dITR.RC construct and their effect on its replicative activity and on its encapsidation are analyzed. The mutations introduced into the RES element are also analyzed for their effect on the encapsidation of a CMV-LacZ cassette. More specifically, the following genetically modified RES sequences are prepared (FIG. 10):

RES 190–350

RES 281–540

RES 350–540

RES 255–540

RES 190–255/350–540

RES 190–281/350–540

These variants are prepared by conventional techniques, using restriction enzymes and ligases. The nucleotide positions are given with reference to the sequence of FIG. 8 (SEQ ID NO: 8 and 9).

Figure 10:
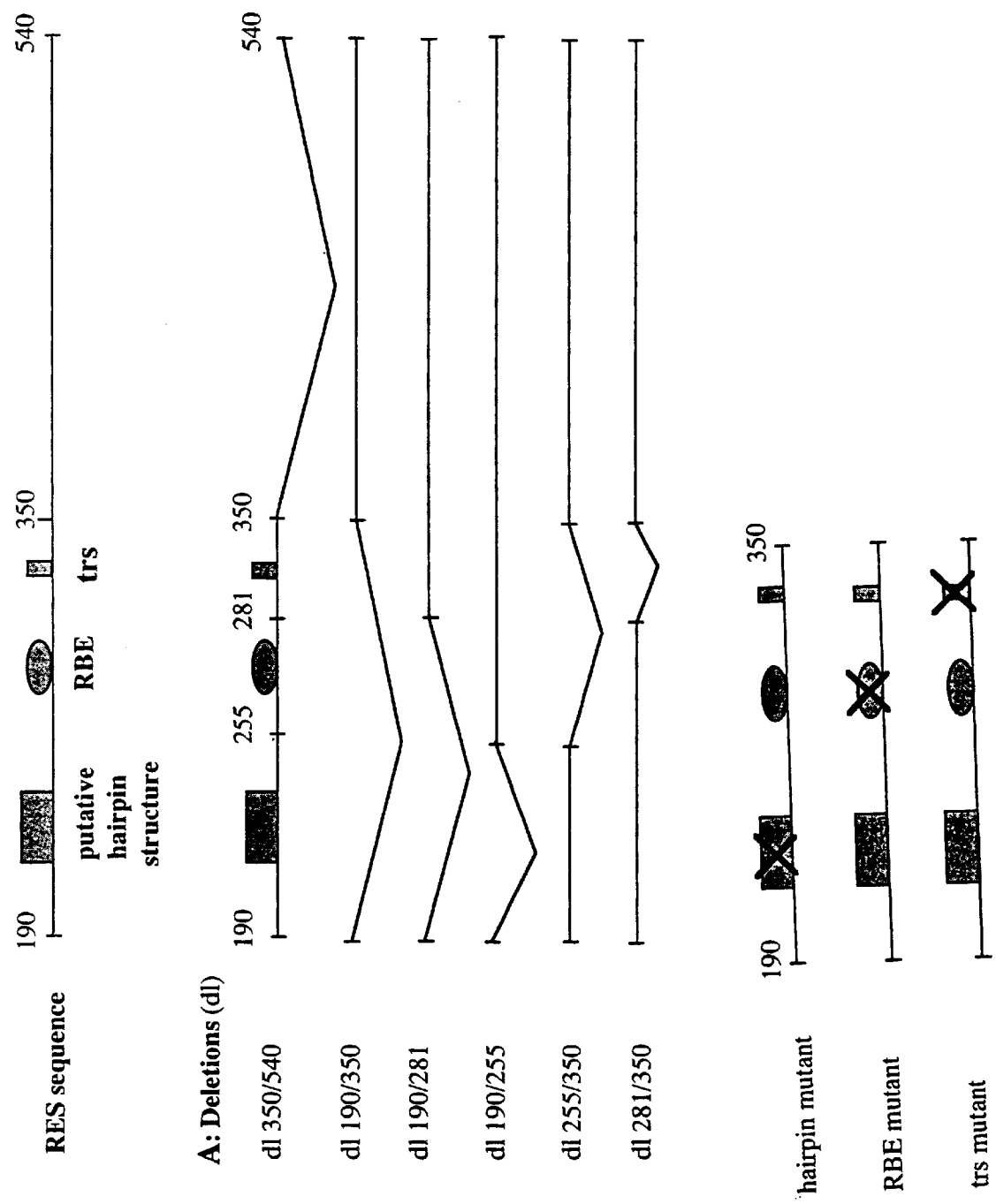
FIG. 10: Representation of deleted and mutated RES elements. Only the mutation introduced in the 190–350 fragment are represented. Simultaneous mutations at various positions can also be done.

Additional modified RES sequences are produced, comprising one or more mutations, as compared to the sequence of FIG. 2. More preferably, these RES variants comprise mutations outside of the functional palindromic, RBE and trs domains. Particular examples of mutated elements are represented in FIG. 10.

5.6. Design of New Trans-complementing Rep-cap Plasmids Able to Provide the Viral Functions for Particle Formation but Unable to Recombine with the New RES+ AAV Vectors (ITR-RES-transgene-ITR)

In order to further avoid any potential homologous recombination events between the RES element of the rAAV plasmid vector and the rep gene present in the rep-cap plasmids, the following constructions are made.

5.6.1 Deletion of the RES Minimal Elements from the Rep-cap Genome

If no deleterious effects are observed on the expression of the rep and cap genes, a first construction is a rep-cap plasmid devoid of any overlapping region with RES. For instance, a Rep-Cap plasmid having a rep-cap unit with a 5' end starting at nucleotide position 300 of the AAV genome can be prepared, and used to produce a rAAV comprising a 5' ITR-RES unit consisting of nucleotides 1-299 of the AAV genome. Such Rep-Cap plasmids usually comprise a heterologous promoter instead of p5.

5.6.2 Use of Non-homologous RES Sequences in the rAAV Vector

A second approach is based on the use of altered RES elements lacking significant homology with the Rep-Cap plasmid. For that purpose, mutation variants of RES can be prepared as described in Example 5.5, having reduced sequence homology with any potentially overlapping region present in the rep-cap plasmid. Also, artificial RES elements can be prepared by removing most non-essential sequences.

As a further alternative, non-homologous RES sequences can also be used, i.e., RES elements derived from other parvoviruses, with no significant sequence homology to the AAV genome, but which are functional.

6. Assay of rAAV Transducing Activity in Vitro and Vivo

To relate the RCA and the dot blot titers to the in vitro transducing activity of rAAV, we used a vector encoding the nlsLacZ gene under the control of the CMV promoter. Two large scale stocks of rAAVCMVnlsLacZ, produced either with adenovirus (vAd) or with the pAdc adenoviral plasmid, were assayed in vitro in an infectious LacZ Forming Unit assay (LFU) on HeLa cells (Table 4). Typically, a ratio ranging from 10 to 50 was observed between the infectious particles and the LacZ forming units (LFU) measured on HeLa cells in the presence of adenovirus. This ratio was further increased ten fold if the LFU assay was performed in the absence of adenovirus. The particles to LFUs ratio ranges for both rAAV stocks from $4 \times 10^2$ to $6 \times 10^2$. These data indicate that, at least in vitro, rAAV produced with either adenovirus or an adenoviral plasmid is functional. Further in vitro assays also indicate that the rAAVCM-VnlsLacZ virus produced with the pAdc plasmid is, as generally described for rAAV, resistant to heat treatment (30 mn at 56° C.), to repeated freeze and thaw (at least twice), and is also stable at least three days at 4° C. (data not shown).

A different sensitivity between these two assays, the RCA and the LFU, can explain the discrepancy between the number of infectious and transducing particles (Couffinhal et al., 1997). However two other hypothesis can also be evoked: i) not all the rAAV genomes able to replicate and thus detected in the RCA, can lead to the production of the LacZ protein 24 hours after infection; ii) the Rep proteins produced in the HeLaRC32 cells, used for the RCA but absent in the control HeLa cells used for the LFU assay, account for this difference. To test this last hypothesis, rAAVCMVnlsLacZ was used to infect either HeLa or HeLaRC32 cells in the presence or absence of adenovirus, followed by an X-Gal staining 24 hours later. LFU titers remained essentially unchanged using the HeLaRC32 cells as compared with control cells. This result indicates that even in the presence of Rep proteins, the rAAV titer as measured by the LFU assay is not equivalent to the number of infectious particles measured by the RCA.

Figure 6:
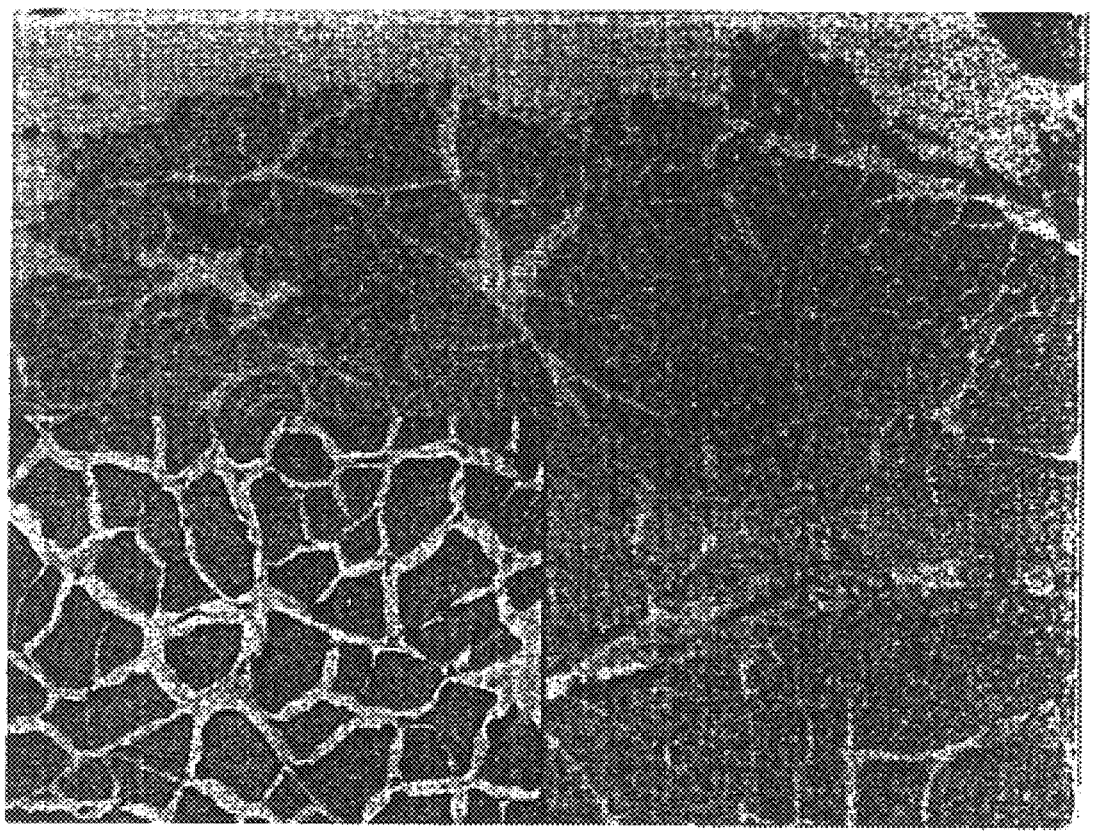
FIG. 6: Nuclear targeted β-galactosidase expression in the rat muscle after injection of rAAVCMVnlsLacZ. Tibialis anterior muscles of three 9 weeks-old Wistar rats were injected with 2.5 10$^8$ rAAVCMVnlsLacZ infectious particles each (three sites of injection per muscle). Animals were sacrificed 4 weeks after injection. Muscles were fixed with paraformaldehyde, stained overnight at 37° C. with X-Gal, paraffin embedded and sectioned into 4-μm sections which were counterstained with Kernechtrot solution. (magnifications: panel×100; inset panel×600).

To test the in vivo transducing activity of rAAVCM-VnlsLacZ (produced with the pAdc plasmid), $2.5 \times 10^8$ infectious particles (measured by RCA) were injected in the rat tibialis anterior muscle (three animals were injected). Animals were sacrificed one month post injection and X-gal staining revealed the presence of transduced fibers in most of the tissue sections (FIG. 6). Transduction efficiency was evaluated to range between 10–20% of the fibers.

Other in vivo data were obtained after injection in the mouse muscle of rAAV encoding the murine erythropoietin (mEpo) under the control or not of a doxycycline inducible promoter (Bohl D. et al., Blood, 92 (1998) 1512). Two different vectors were used in this study: i) the rAAVCMVEpo/rtTa (produced with adenovirus) which harbors the mEpo cDNA under the control of the tetO-CMV promoter, as well as the reverse transactivator (rtTA) under the control of the Moloney LTR. This vector was injected into the tibialis anterior muscle of mice ($2.1 \times 10^9$ or $4.2 \times 10^9$ infectious particles/muscle) and transgene expression was monitored by measuring Epo secretion and increase of the hematocrit. The data obtained up to 7 months after injection, indicate that Epo secretion can be switched on and off depending on the presence or absence of doxycycline in the drinking water; ii) Epo secretion was also achieved after injection in the mouse muscle of rAAVCMVEpo (produced with the pAdc adenoviral plasmid) in which the mEpo cDNA is placed under the control of the Moloney LTR. In summary, these in vivo data indicate that rAAV produced with adenovirus or the adenoviral plasmid, pAdc, is functional.

Discussion

Because of some unique properties among viral vectors, the use of rAAV for gene transfer is becoming widespread. However, efficient production of these vectors still relies upon methods which are cumbersome and have to be performed at a large scale in order to obtain a sufficient amount of virus. Furthermore, the need for helper adenovirus for rAAV assembly, leads to the concomitant production of adenoviral particles which are difficult to separate from rAAV particles. The present invention now provides novel methods and compositions for improved production and characterization of rAAV stocks.

A first major technical improvement of this invention is the centrifugation step needed to purify rAAV. By changing the CsCl gradient conditions, we considerably shortened the protocol since equilibrium in the gradient can be reached by centrifuging 6 hours instead of 48 hours as previously described. Alternatively, or in combination therewith, the use of chromatography or affinity columns should further improve the rAAV purification procedure (Tamayose et al., 1996).

The second improvement described in this study is the characterization of rAAV stocks. In many studies, titers, and consequently m.o.i., are given as genome particles per ml (measured by dot blot). This parameter does not provide information on the rAAV infectivity and on the level of contamination with adenovirus and rep-positive AAV. The lack of these information when performing in vitro and in vivo experiments, using total cellular extracts or purified virus, makes any comparative evaluation of rAAV-mediated gene transfer quite difficult. We developed a general titration method based on the use of an HeLa rep-cap stable cell line. This method can be applied to any viral stock produced whichever transgene is present. It can also be applied to monitor (measure) viral safety issues in biological fluids, after in vivo administration of a rAAV preparation in animals and/or human subjects. It allows the measurement of infectious rAAV particles as well as of the level of contamination with infectious adenovirus and rep-positive AAV (FIG. 3). In the titration method described by Clark et al. (Clark et al, 1996; Clark et al., 1995), replicative forms were analyzed on a Southern blot, 60 hours after infection of the HeLa rep-cap cells (that is late in the AAV growth cycle) with different dilutions of rAAV and adenovirus. In our assay, cells are individually analyzed (FIG. 3) for the presence of replicating rAAV DNA 24 hours after infection, which is the minimal time to allow replication of viral DNA but is short enough to prevent the virus from being released in the culture medium, spreading to other cells in the well (Carter, 1990). In addition, in the titration assay developed by Clark et al. (1996), measurements of the level of contamination with adenovirus and rep-positive AAV were lacking. The RCA of the present invention provides for the first time information regarding (i) infectious rAAV particles, (ii) adenovirus contamination and (iii) rep-positive rAAV contamination.

The number of infectious particles measured by our RCA is approximately 50 fold higher than the number of transducing particles as measured for example by the LacZ forming units with the rAAVCMVnlsLacZ (Table 4). Whether this difference is linked to the assay used to detect transgene expression or to a general property of rAAV remains still unclear. It is possible that only part of the pool of replicating DNA is available for transgene expression, at least in vitro. Another possibility is the presence in the rAAV stock of defective interfering genomes which, as described for wild type AAV, would have internal deletions and still retain the viral ITRs (Carter et al., 1979; Laughlin et al., 1979).

This RCA was used to carefully monitor the effect of two major modifications introduced in the rAAV production protocol: 1) the use of different rep-cap expression plasmids; 2) the replacement of adenovirus by an adenoviral plasmid.

The study by Samulski et al (1989) describes the pAAV/Ad plasmid as more efficient than a plasmid without the adenoviral ITR. Yields were assessed by looking at rAAV transducing activity (conferring neomycin resistance) using a non purified cell lysate. Our results obtained with different rAAV vectors produced on large scale and purified through a cesium gradient clearly do not confirm this initial observation. Indeed, surprisingly, not only the total particles yield was not affected but also the number of infectious particles was increased when the two adenoviral ITRs were removed from the rep-cap construct. Indeed, in all the rAAV stocks produced with the pspRC plasmid, the particles to infectious particles ratios were always inferior to 50, while they ranged between $10^3$ and $10^4$ in the rAAV stocks produced with the pAAV/Ad plasmid (Table 1).

Rep and Cap proteins level are an important parameter to consider for rAAV production. In our production protocol, Rep and Cap proteins can be expressed under the control of either the native AAV promoters or heterologous promoters. In particular, expression of rep can be controlled by:

(i) the native AAV p5 and p19 promoters (pspRC construct). This configuration was chosen to preserve, as much as possible, the natural cascade of trans-activations and/or repressions occurring during AAV life cycle in the presence of adenovirus (Pereira et al., 1997);

(ii) a heterologous promoter, to produce low levels of rep and/or inactivate potential RES sequences present in this region.

Expression of Cap proteins can also be regulated either by:

(i) the native AAV p40 promoter (pspRC construct), or (ii) a heterologous promoter, such as CMV (pspRCC construct), to provide for a strong expression of Cap proteins. Indeed, at the opposite of Rep, overexpression of CAP proteins by using an heterologous promoter has also been shown to increase the rAAV yield (Vincent et al., 1997).

Preferred rep-Cap constructs, however, comprise native AAV promoters, optionally modified in order to inactivate potential RES sequences.

Another preferred characteristic of the rAAV production method of this invention resides in the replacement of adenovirus with an adenoviral plasmid. Two constructs were tested: one harboring the entire adenoviral genome and the second harboring deletions of the ITRs, the Ψ and E1 regions (FIG. 1C). Despite the large size of these plasmids (over 40 kb), rAAV production was not decreased after transfection into 293 cells. rAAV obtained under these conditions displayed the same physical properties than rAAV produced with adenovirus (infectious particles to LFU ratio and heat stability). Recently, other investigators have also described the rAAV production using adenoviral plasmids which harbor either an E1 deleted adenoviral genome or only the minimal adenoviral functions needed for rAAV production (Grimm D. et al., 1998) (Ferrari et al., 1997). In our hands, all rAAV stocks but two obtained using the pAdc plasmid were free of detectable adenoviral contamination as determined by RCA.

In vivo experiments using rAAV produced with the pAdc plasmid indicate that these viruses are competent for transducing muscle cells in mice and rats. It is possible, however, that this relatively pure rAAV displays a different kinetic and transduction efficiency in vivo as compared to rAAV produced with adenovirus.

Contamination of the rAAV stocks with rep-positive AAV is a challenging issue. Indeed, some studies (Allen et al., 1997; Halbert et al., 1997) have reported that rAAV preparation are contaminated with such particles revealed either by RCA or by dot blot using in both cases a rep-cap probe. The extent of contamination published ranges from 0.0001 to 10% of the rAAV stocks. In the study of Allen et al (1997), the contaminating rep-positive AAV has been characterized following sequential amplification in adenovirus-infected cells. All rep-positive AAV genomes sequenced have at least a portion of the AAV ITRs and a non homologous recombination leading to the insertion of rep-cap sequences close to AAV ITRs was proposed to explain the emergence of such contaminant (Allen et al., 1997).

Our RCA assay indicates that amplification of the vector can occur in HeLa cells, in the presence of adenovirus. Furthermore, replicative forms were also detected in low molecular weight DNA extracted from rAAV and adenovirus-infected 293 cells (FIG. 5). Both these observations suggest the presence of rep-positive particles in rAAV stocks. The extent of this contamination, however, represents on average 0.001% of infectious rAAV particles (also measured by RCA), which seems much lower than in rAAV stocks prepared with previous methods.

REFERENCES

ALLEN, J. M., DEBELAK, D. J., REYNOLDS, T. C. AND MILLER, A. D. (1997). Identification and elimination of replication-competent Adeno-Associated Virus (AAV) that can arise by non homologous recombination during AAV vector production. J. Virol. 71, 6816–6822.

CARTER, B. J. (1990). The growth cycle of adeno-associated virus. In *Handbook of Parvoviruses*. P. Tjissen, eds (CRC Press, Boca Raton, Fla.) pp.155–168.

CARTER, B. J., LAUGHLIN, C. A., DE LA MAZA, L. M. AND MYERS, M. (1979). Adeno-associated virus auto-interference. Virology 92, 449.

CLARK, K. R., VOULGAROPOULOU, F. AND JOHNSON, P. R. (1996). A stable cell line carrying adenovirus-inducible rep and cap genes allows for infectivity titration of adeno-associated virus vectors. Gene Ther. 3, 1124–1132.

CLARK, K. R., VOULGAROPOULOU, F., FRALEY, D. M. AND JOHNSON, P. R. (1995). Cell lines for the production of recombinant adeno-associated virus. Hum. Gene Ther. 6, 1329–1341.

COUFFINHAL, T., KEARNEY, M., SULLIVAN, A., SILVER, M., TSURUMI, Y. AND ISNER, J. M. (1997). Histochemical staining following LacZ gene transfer underestimates transfection efficiency. Hum. Gene Ther. 8, 929–934.

FERRARI, F. K., XIAO, X., McCARTHY, D. AND SAMULSKI, R. J. (1997). New developments in the generation of Ad-free, high-titer rAAV gene therapy vectors. Nature Med. 3, 1295–1297.

FISHER, K. J., JOOSS, K., ALSTON, J., YANG, Y., HAECKER, S. E., HIGH, K., PATHAK, R., RAPER, S. E. AND WILSON, J. M. (1997). Recombinant adeno-associated virus for muscle directed gene therapy. Nature Med. 3, 306–312.

FLANNERY, J. G., ZOLOTUKHIN, S., VAGUERO, M. I., LA VAIL, M. M., MUZYCZKA, N. AND HAUSWIRTH, W. W. (1997). Efficient photoreceptor-targeted gene expression in vivo by recombinant adeno-associated virus. Proc. Natl. Acad. Sci. USA 94, 6916–6921.

GINSBERG, H. S., LUNDHOLM, U. AND LINNE, T. (1977). Adenovirus DNA-binding protein in cells infected with wild-type 5 adenovirus and two DNA-minus, temperature-sensitive mutants, H5ts 125 and H5ts 149. J. Virol. 23, 142–151.

GRAHAM, F. L. AND PREVEC, L. (1991). Manipulation of adenovirus vectors. In *Gene Transfer and Protocol*. .E. J. Murray, eds (The Humana Press, Inc., Clifton, N.J.) pp.109–128.

GRIMM D., KERN A., RITTNER K., KLEINSCHMIDT (1998). Novel tool for production and purification of recombinant adenoassociated virus vectors. Hum. Gene. Ther. 9, 2745–2760.

HALBERT, C. L., STANDAERT, T. A., AITKEN, M. L., ALEXANDER, I. E., RUSSELL, D. W. AND MILLER, A. D. (1997). Transduction by Adeno-Associated Virus vectors in the rabbit airway: efficiency, persistence and readministration. J. Virol. 71, 5932–5941.

HERZOG, R. W., HAGSTROM, J. N., KUNG, S.-H., TAI, S. J., WILSON, J. M., FISHER, K. J. AND HIGH, K. A. (1997). Stable gene transfer and expression of human blood coagulation factor IX after intramuscular injection of recombinant adeno-associated virus. Proc. Natl. Acad. Sci. USA 94, 5804–5809.

KESSLER, P. D., PODSAKOFF, G. M., CHEN, X., MCQUISTON, S. A., COLOSI, P. C., MATELIS, L. A., KURTZMAN, G. J. AND BYRNE, B. J. (1996). Gene delivery to skeletal muscle results in sustained expression and systemic delivery of a therapeutic protein. Proc. Natl. Acad. Sci. USA 93, 14082–14087.

KOEBERL, D. D., ALEXANDER, I. E., HALBERT, C. L., RUSSELL, D. W. AND MILLER, A. D. (1997). Persistent expression of human clotting factor IX from mouse liver after intravenous injection of adeno-associated virus vectors. Proc. Natl. Acad. Sci. USA 94, 1426–1431.

LAUGHLIN, C. A., MYERS, M. W., RISIN, D. L. AND CARTER, B. J. (1979). Defective-interfering particles of the human parvovirus adeno-associated virus. Virology 94, 162.

LEONARD, C. J. AND BERNS, K. I. (1994). Adeno-associated virus type 2: a latent life cycle. Prog. Nucleic Acid Res. Mol. Biol. 48, 29–53.

LI, J., SAMULSKI, R. J. AND XIAO, X. (1997). Role for highly regulated rep gene expression in adeno-associated virus vector production. J. Virol. 71, 5236–5243.

MCLAUGHLIN, S. K., COLLIS, P., HERMONAT, P. L. AND MUZYCZKA, N. (1988). Adeno-associated virus general transduction vectors: analysis of proviral structures. J. Virol. 62, 1963–1973.

MUZYCZKA, N. (1992). Use of adeno-associated virus as a general transduction vector for mammalian cells. Curr. Top. Microbiol. Immunol. 158, 97–129.

PEREIRA, D. J., McCARTY, D. M. AND MUZYCZKA, N. (1997). The adeno-associated virus (AAV) rep protein acts as both a repressor and an activator to regulate AAV transcription during a productive infection. J. Virol. 71, 1079–1088.

SAMULSKI, R. J., CHANG, L. S. AND SHENK, T. (1989). Helper-free stocks of recombinant adeno-associated viruses: normal integration does not require viral gene expression. J. Virol. 63, 3822–3828.

SNYDER, R., XIAO, X. AND SAMULSKI, R. J. (1996). Production of recombinant adeno-associated viral vectors. In *Current Protocols in Human Genetics*. N. Dracopoli, J. Haines, B. Krof, D. Moir, C. Morton, C. Seidman, J. Seidman and D. Smith, eds (John Wiley and Sons Publisher, New York, N.J.) pp.12.1.1–12.1.23.

SNYDER, R. O., MIAO, C. H., PATIJN, G. A., SPRATT, S. K., DANOS, O., NAGY, D., GOWN, A. M., WINTHER, B., MEUSE, L., COHEN, L. K., THOMPSON, A. R. AND KAY, M. A. (1997). Persistent and therapeutic concentrations of human factor IX in mice after hepatic gene transfer of recombinant AAV vectors. Nature Genet. 16, 270–276.

TAMAYOSE, K., HIRAI, Y. AND SHIMADA, T. (1996). A new strategy for large-scale preparation of high-titer recombinant adeno-associated virus vectors by using packaging cell lines and sulfonated cellulose column chromatography. Hum. Gene Ther. 7, 507–513.

VINCENT, K. A., PIRAINO, S. T. AND WADSWORTH, S. C. (1997). Analysis of recombinant Adeno-Associated Virus packaging and requirements for rep and cap gene product. J. Virol. 71, 1897–1905.

XIAO, X., LI, J. AND SAMULSKI, R. J. (1996). Efficient long-term gene transfer into muscle tissue of immunocompetent mice by adeno-associated virus vector. J. Virol. 70, 8098–8108.

YAKOBSON, B., KOCH, T. AND WINOCOUR, E. (1987). Replication of adeno-associated virus in synchronized cells without the addition of helper virus. J. Virol. 61, 972–981.

ZOLOTUKHIN, S., POTTER, M., HAUSWIRTH, W. W., GUY, J. AND MUZYCZKA, N. (1996). A "humanized" green fluorescent protein cDNA adapted for high-level expression in mammalian cells. J. Virol. 70, 4646–4654.

TABLE 2

|  | part/ml[1] | inf.part./ml[2] | LFU/ml[3] |
|---|---|---|---|
| pspRC | $1.7 \cdot 10^{10}$ | $1.2 \cdot 10^9$ | $2.0 \cdot 10^6$ |
| pIM45 | $8.5 \cdot 10^9$ | $3.2 \cdot 10^8$ | $6.6 \cdot 10^5$ |
| RepCMVCap | $3.4 \cdot 10^{10}$ | $5.8 \cdot 10^8$ | $2.0 \cdot 10^6$ |

TABLE 3

|  | 72 hrs | | 96 hrs | | 120 hrs | |
|---|---|---|---|---|---|---|
|  | part/ml[1] | inf.part/ml[2] | part/ml[1] | inf.part/ml[2] | part/ml[1] | inf.part/ml[2] |
| pAdc | $3.5 \cdot 10^{10}$ | $1.4 \cdot 10^9$ | $2.5 \cdot 10^{10}$ | $6.0 \cdot 10^8$ | $2.1 \cdot 10^{10}$ | $3.5 \cdot 10^7$ |
| pAdΔ | $3.5 \cdot 10^{10}$ | $2.2 \cdot 10^9$ | $2.0 \cdot 10^{10}$ | $1.2 \cdot 10^9$ | $2.5 \cdot 10^{10}$ | $1.0 \cdot 10^8$ |

TABLE 4

|  | part/ml[1] | inf. part/ml[2] | LFU/ml[3] (+wtAd5) | LFU/ml[3] (−wtAd5) | part/ inf. part | inf. part/ LFU |
|---|---|---|---|---|---|---|
| vAd | $1.7 \cdot 10^{11}$ | $6.6 \cdot 10^9$ | $4.1 \cdot 10^8$ | ND | 25 | 16 |
| pAdc | $3.0 \cdot 10^{11}$ | $2.5 \cdot 10^{10}$ | $5.0 \cdot 10^8$ | $1.4 \cdot 10^7$ | 12 | 50 |

TABLE 1

| vector name | size (b) | rep-cap plasmid | Virus or plasmid | rAAV Titer p./ml[1] | rAAV Titer i.p./ml[2] | ratio | Contaminations[3] Ad. i.p./ml | Contaminations[3] rep+ AAV i.p./ml | Vol. (ml) |
|---|---|---|---|---|---|---|---|---|---|
| AAVCMVLacZ | 4873 | pAAV/Ad | wtAd5 | $1.2 \cdot 10^{12}$ | $1.0 \cdot 10^9$ | $1.2 \cdot 10^3$ | $5 \cdot 10^4$ | $4.5 \cdot 10^7$ | 1.6 |
| AAVCMVGDNF | 3000 | pAAV/Ad | wtAd5 | $2.5 \cdot 10^{11}$ | $1.5 \cdot 10^7$ | $1.7 \cdot 10^4$ | $7.5 \cdot 10^4$ | $5.5 \cdot 10^5$ | 1.7 |
| AAVCMVGDNF | 3000 | pAAV/Ad | wtAd5 | $8.0 \cdot 10^{11}$ | $2.0 \cdot 10^8$ | $4.0 \cdot 10^3$ | $1.0 \cdot 10^5$ | $4.0 \cdot 10^7$ | 2.8 |
| AAVCMVLacZ | 4873 | pspRC | wtAd5 | $1.6 \cdot 10^{12}$ | $9.2 \cdot 10^{10}$ | 17.3 | $7 \cdot 10^3$ | $1.0 \cdot 10^5$ | 1.1 |
| AAVPGKβGLU | 3854 | pspRC | Ad.dts | $3.0 \cdot 10^{11}$ | $9.5 \cdot 10^9$ | 31.5 | $3.1 \cdot 10^4$ | $1.0 \cdot 10^5$ | 3.0 |
| AAVPGKhALD | 3565 | pspRC | Ad.dts | $1.4 \cdot 10^{11}$ | $1.8 \cdot 10^{10}$ | 7.8 | $1.3 \cdot 10^4$ | $1.0 \cdot 10^4$ | 3.1 |
| AAVCMVApoE4 | 2609 | pspRC | wtAd5 | $4.7 \cdot 10^{10}$ | $1.1 \cdot 10^{10}$ | 4.2 | $1.1 \cdot 10^4$ | $1.5 \cdot 10^4$ | 3.6 |
| AAVCMVEpo/rtTa | 5017 | pspRC | wtAd5 | $2.5 \cdot 10^{11}$ | $2.1 \cdot 10^{10}$ | 11.9 | $2.3 \cdot 10^4$ | $1.3 \cdot 10^6$ | 4.1 |
| AAVPGKnlsLacZ | 4712 | pspRC | wtAd5 | $2.5 \cdot 10^{11}$ | $9.0 \cdot 10^{10}$ | 2.8 | $2.2 \cdot 10^4$ | $5.0 \cdot 10^5$ | 4.2 |
| AAVCMVnlsLacZ | 4641 | pspRC | pAdc | $5.1 \cdot 10^{11}$ | $1.6 \cdot 10^{10}$ | 31.8 | $<5 \cdot 10^2$ | $4.5 \cdot 10^5$ | 7.6 |
| AAVLTRApoE | 3700 | pspRC | pAdc | $3.0 \cdot 10^{11}$ | $3.7 \cdot 10^{10}$ | 8.1 | $2.5 \cdot 10^3$ | $5.5 \cdot 10^5$ | 7.6 |
| AAVLTREpo | 3310 | pspRC | pAdc | $3.7 \cdot 10^{11}$ | $4.2 \cdot 10^{10}$ | 8.8 | $<5 \cdot 10^2$ | $4.0 \cdot 10^5$ | 7.2 |
| AAVCMVnlsLacZ* | 4641 | pspRC | pAdc | $3.0 \cdot 10^{11}$ | $2.5 \cdot 10^{10}$ | 12.0 | $<5 \cdot 10^2$ | $7.0 \cdot 10^4$ | 13.4 |
| AAVCMVβGLU | 4717 | pspRC | pAdc | $3.8 \cdot 10^{10}$ | $1.5 \cdot 10^{10}$ | 2.5 | $<5 \cdot 10^2$ | $4.5 \cdot 10^4$ | 6.8 |
| AAVCMVEpo | 2238 | pspRC | pAdc | $1.2 \cdot 10^{11}$ | $5.4 \cdot 10^{10}$ | 2.2 | $<5 \cdot 10^2$ | $5.0 \cdot 10^4$ | 6.9 |
| AAVCMVvEGF | 2080 | pspRC | pAdc | $1.8 \cdot 10^{11}$ | $7.4 \cdot 10^{10}$ | 2.4 | $<5 \cdot 10^2$ | $2.5 \cdot 10^5$ | 7.5 |
| AAVCMVnlsLacZ* | 4641 | pspRC | pAdc | $7.8 \cdot 10^{10}$ | $5.5 \cdot 10^{10}$ | 1.4 | $<5 \cdot 10^2$ | $1.5 \cdot 10^5$ | 14.0 |
| AAVCMVβGLU* | 4717 | pspRC | pAdc | $3.4 \cdot 10^{11}$ | $6.6 \cdot 10^{10}$ | 5.1 | $2.5 \cdot 10^3$ | $1.3 \cdot 10^5$ | 11.4 |

What we claim is:

1. A method of characterizing a rAAV preparation, said method comprising:
   a) contacting a sample of said preparation with a culture of cells expressing the rep proteins,
   b) contacting a sample of said preparation with a culture of cells expressing the rep proteins, co-infected with an adenovirus, and
   c) contacting a sample of said preparation with a culture of cells which do not express Rep proteins, co-infected with an adenovirus,
   and measuring the presence of viruses in cultures a), b) and c).

2. The method of claim 1, wherein the culture of cells in a), b) and c) is a culture of human primary cells or established cell line.

3. The method of claim 1, wherein the cells of a) and b) express the rep proteins encoded by nucleotides 190–2278 of the AAV genome.

4. The method of claim 1, wherein the cells further express the cap proteins of AAV.

5. The method of claim 1, wherein the cell cultures in a), b) and c) is a culture of HeLa cells.

6. The method of claim 1, wherein the measuring of the presence of viruses comprises the determination of the presence of rAAV.

7. A method of producing rAAV preparations, comprising:
   a) producing rAAVs in a cell culture expressing Rep and Cap functions and adenovirus helper functions, and
   b) characterizing the rAAVs produced according to the method of claim 1.

8. A method of producing rAAV preparations, comprising:
   a) producing rAAVs in a cell culture expressing Rep and Cap functions and adenovirus helper functions,
   b) purifying the rAAVs produced, and
   c) characterizing the rAAVs produced according to the method of claim 1.

9. The method of claim 1, for detecting the presence of rAAV, rep-positive AAV and/or adenoviruses in a biological fluid.

10. The method of claim 6, wherein determining the presence of rAAV comprises determining the presence of AAV replicating nucleic acid within the cells.

11. The method of claim 10, wherein determining the presence of AAV replicating nucleic acid is performed by hybridization of the cellular nucleic acids with a probe complementary to all or part the rAAV genome.

12. The method according to claim 7, wherein step a) comprises the co-transfection of a cell culture with a rep-cap plasmid, a rAAV vector plasmid and a helper adenovirus.

13. The method according to claim 7, wherein step a) comprises the use of at least one adenovirus helper plasmid, instead of helper adenovirus.

14. The method according to claim 7, wherein, in the producing step a), a rep-cap plasmid is used, which lacks any functional ITR region.

15. The method according to claim 7, wherein, in the producing step a), a culture of cells which contain, in their genome, nucleic acid construct(s) encoding the rep and/or cap functions.

16. The method according to claim 7, wherein the rAAV comprise one or several RES elements.

17. The method according to claim 8, wherein step b) comprises the purification of the rAAV produced by centrifugation, clarification, cesium chloride gradient purification and/or chromatography.

18. The method according to claim 8, wherein in step b, a method of purifying rAAVs from a biological sample is used, which comprises treating said sample in a cesium chloride gradient centrifugation at between 60,000 and 70,000 rpm, and recovering the fraction(s) containing the purified rAAVs.

19. The method according to claim 8, wherein in step b, a method of purifying rAAVs from a biological sample is used, which comprises treating said sample at least by anion exchange chromatography combined with exclusion chromatography.

20. The method according to claim 12, wherein a rep-cap plasmid is pspRC or pspRCC.

21. The method according to claim 13, wherein an adenovirus helper plasmid is pAdc or pAdΔ.

22. The method according to claim 14, wherein the Rep-Cap plasmid contains a Rep-Cap unit consisting of residues 190–4484 of the AAV genome or fragments thereof encoding functional Rep and Cap proteins.

23. A method of producing rAAVs comprising:
   (i) co-transfecting a cell culture with:
      a Rep-Cap plasmid devoid of ITR, containing a Rep-Cap unit consisting of residues 190–4484 of the AAV genome or fragments thereof encoding functional Rep and Cap proteins, and
      an adenovirus plasmid containing the entire adenoviral genome or a genome lacking the left and right ITRs, the packaging region and, optionally, the E1 region, and (ii) recovering the rAAV produced;

wherein the rAAV vector plasmid comprises one or several RES elements, in a sense or antisense orientation.

24. A method of producing rAAVs comprising:
   (i) co-transfecting a culture of cells which contain, in their genome, nucleic acid construct(s) encoding the rep and/or cap functions, with:
      a rAAV vector plasmid, and
      a helper adenovirus or an adenovirus plasmid containing the entire adenoviral genome or a genome lacking the left and right ITRs, the packing region and, optionally, the E1 region, and (ii) recovering the rAAV produced; wherein the rAAV vector plasmid comprises one or several RES elements, in a sense or antisense orientation.

* * * * *